United States Patent [19]
Kim et al.

[11] Patent Number: 6,045,800
[45] Date of Patent: Apr. 4, 2000

[54] COMPOSITION FOR PREVENTING OR TREATING PERIODONTAL DISEASES COMPRISING EXTRACT FROM *ACHYRANTHIS RADIX* OR *ULMUS CORTEX*

[75] Inventors: Moon Moo Kim; Sang Nyun Kim; Jae Kyun Seok; Kyung Chul Choi, all of Daejeon, Rep. of Korea

[73] Assignee: LG Chemical Ltd., Seoul, Rep. of Korea

[21] Appl. No.: 09/031,063

[22] Filed: Feb. 26, 1998

[30] Foreign Application Priority Data

Oct. 2, 1997 [KR] Rep. of Korea ............... 97-51004
Dec. 5, 1997 [JP] Japan ..................... 9-336204

[51] Int. Cl.⁷ .......................................... A61K 7/26
[52] U.S. Cl. .................... 424/195.1; 514/900; 514/902
[58] Field of Search ................. 424/195.1; 514/900, 514/902

[56] References Cited

U.S. PATENT DOCUMENTS 5,230,895  7/1993  Czarnecki et al. .

FOREIGN PATENT DOCUMENTS 05 28468A1  2/1993  European Pat. Off. .

OTHER PUBLICATIONS

CA: 1996:69673 Lee et al "The Influence of Methanol Extract of *Ulmus davidiana* . . . " 1995.

BA 94:12460 Pan et al Shoyakugaku Zasshi (1992) 46(2), 131–135.

CA: 96:523 Girach et al Int. J. Pharmacog. (1994) 32(3) 274–283.

CA 92:50252 Forestieri et al Pharm. Res. Commun. Suppl. (1988) 20(5) 33–36.

*Primary Examiner*—Peter F. Kulkosky
*Attorney, Agent, or Firm*—Birch, Stewart, Kolasch & Birch, LLP

[57] ABSTRACT

The present invention provides a composition for preventing or treating periodontal diseases comprising an extract of *Achyranthis radix, Ulmus cortex* or a mixture thereof which inhibits the productions of superoxide, prostaglandin, and interleukin (IL-1β) which are inducers for periodontal diseases and inhibits the enzyme activity of collagenase which decomposes collagen protein which is a substrate for the periodontal tissues, and at the same time promotes collagen protein synthesis, thereby treating periodontal diseases efficiently.

17 Claims, No Drawings

COMPOSITION FOR PREVENTING OR TREATING PERIODONTAL DISEASES COMPRISING EXTRACT FROM *ACHYRANTHIS RADIX* OR *ULMUS CORTEX*

TECHNICAL FIELD

The present invention relates to a composition for preventing or treating periodontal diseases comprising an extract from *Achyranthis radix* or *Ulmus cortex*. More specifically, the present invention relates to a composition for preventing or treating periodontal diseases comprising at least one of an extract from *Achyranthis radixor Ulmus cortex* as an active component which has an excellent therapeutic effect against periodontal diseases. The composition according to the present invention includes a dentifrice composition and an ointment composition.

BACKGROUND ART

Periodontal diseases are referred to as those resulting in gingivitis or periodontitis together with the loss of teeth due to a bleeding, the formation of gingival crevices and the destruction of alveolar bones, etc. These periodontal diseases are progressed by a series of processes comprising colony formation by the periodontal disease-inducing bacteria, the penetration of the bacteria into the gingival tissues and the destruction of the gingival tissues. Briefly, salivary proteins in the saliva within oral cavity are first adsorbed to the surfaces of dentin and cement to form pellicle, and bacteria such as Streptococcus, Actinomyces, etc. are then grown on the surface of the pellicle to form a plaque. As time passes, such a plaque moves to the direction of the periapical root and at the same time anaerobic gram-negative bacteria such as Porphyromonas and Actinobacillus are grown by which these bacteria, bacterial components and bacterial metabolites are penetrated into gingival conjunctive tissues via gingival pocket epithelia to form gingival crevices. As a result of the metabolism by these bacteria, toxins such as hydrogen sulfide, ammonia, and amine which are toxic to the periodontal tissues are secreted and the tissues are directly destructed by the endotoxin such as lipopolysaccharide which is a constituting component of cell wall. At the same time, in vivo immune system is stimulated by the endotoxin, and then various kinds of cytokines such as activated oxygens, prostaglandins, leukotrienes, histamine, and interleukins are secreted to the exterior of cells by the various functions of humoral and cell-mediated immune systems to cause gingival inflammation. After collagen which is a substrate for the periodontal tissues is decomposed by the enzyme such as collagenase which is secreted by the bacteria and leukocytes, gums are retracted and periodontal diseases are developed, if these are allowed to lapse without any treatment.

As efforts to prevent the occurence of such periodontal diseases, antibacterial agents such as chlorohexidine gluconate, cetylpyridium chloride, sanguinarine and triclosan (e.g., 5-chloro-2-(2,4-dichlorophenyl)phenol) and anti-inflamnmatory agents such as triamcinolone acetanide have been developed as the agents which can kill the periodontal diseases-inducing bacteria within a short period of time and applied to the oral cavity products such as gargling solutions, dentifrices, and ointments. The oral cavity products developed hitherto, however, have disadvantages that they could not basically prevent the occurence of the periodontal diseases.

Therefore, various efforts to prevent the periodontal diseases have been extensively made in Korea in recent years which use medicinal herbs such as myrrh, *Mori cortex, Cimicifugae rhizoma*, green tea (e.g., *Theae folium*), *Glycyrrhizae radix, Scutellariae radix, Taraxaci radix, Lonicerae flos*, and a maize. However, the extracts of the medicinal herbs which can inhibit the production of prostaglandin which plays a major role in inducing the periodontal diseases or inhibit the activity of collagenase which decomposes the periodontal tissues have not yet been identified up to date. Current methodology is only possible to the extent that the plaque formation is inhibited or the occurrence of the periodontal diseases is inhibited with medicinal herbs which have anti-bacterial, anti-inflamatory, astriction, hemostatic or blood circulation promoting actions.

One of the most widely used methods until now in the treatment of the periodontal diseases is to use pharmaceutically active components which can inhibit the activity of an enzyme, collagenase which decomposes the periodontal tissues, or inhibit the production of prostaglandin which is an inducing agent for the periodontal diseases.

As an example of such method, U.S. Pat. No. 5,230,895 teaches that the periodontal diseases can be treated by inhibiting the enzyme activity of collagenase which decomposes the periodontal tissues using a system by which active components containing tetracycline are continuously delivered. European Laid-Open Publication No. 528 468 A1 suggests a method for treating the periodontal diseases which comprises preventing the periodontal diseases by inhibiting the production of prostaglandin which is an inducing agent of the periodontal diseases using a dentifrice and an oral cleansing agent comprising triclosan.

The pharmacologically active components listed above, however, have a limitation that they do not have both the actions on inhibiting the production of the periodontal disease-inducing agents and on inhibiting the activity of the periodontal tissue-decomposing enzyme in the course of treatment of the periodontal disease, but have either of the actions, and thus, cannot completely treat the periodontal diseases. In addition, there is a concern that various side effects may appear upon long term use of such agents because they are synthetic chemicals. Especially, tetracycline is usually administered in an amount of 1000 mg/day for 5 to 7 days with a dose of 250 mg (1 tablet) with 4 times. It is reported that when tetracycline is administered into a subject, the symptom of the disease is relieved to a clinically normal state, and if tetracycline is administered for a day after removing dental calculus, a considerably significant result is obtained. In view of a report on the long term administration of the agent with a low concentration, after tetracycline is administered with a daily dose of 1000 mg for 2 weeks and subsequently with a daily dose of 250 mg in once for 48 weeks, the results were obtained that gingivitis has clinically decreased, motile bacterial strains have been eliminated from the subgingival plaques and the depth of gingival crevice and the adsorption index that bacteria are adsorbed to the plaques have been decreased. However, if a low concentration of tetracycline is used for a long time, a considerable caution is requested because a drug resistance by gram-negative bacteria occurs frequently and the resistance also occurs frequently even if the administration of the antibiotic is ceased. Further, the use of the antibiotics has a limitation that it frequently induces side effects such as vomiting, a complaint for the ache of gastrointestinal tracts, diarrhea, dental coloring, etc. and thus, a pregnant woman and children should refrain the use of such agent.

SUMMARY OF THE INVENTION

Accordingly, the inventors have conducted an extensive research for many years in order to develop a drug which has no toxic side-effect while shows excellent therapeutic effects on the periodontal diseases even if it is administered to human for a long time, making the various Chinese herbal medicines and plant extracts an object of research by means of scientific methods such as the activity determination for collagenase which decomposes the periodontal tissues, the quantitative analysis of interleukin-1β and prostaglandin ($PGE_2$) which cause the periodontal diseases, the determination of the superoxide production and the quantitative analysis for collagen synthesis, and have screened Chinese herbal medicines and plant extracts which have excellent effects on inhibiting the activity of collagenase or inhibiting the productions of interleukin-1β and prostaglandin while promote the collagen synthesis. As a result, the inventors have discovered that the specific extract of *Achyranthis radix* or *Ulmus cortex* as described below has excellent effects on inhibiting the production of the periodontal disease-inducing agents and at the same time on inhibiting the activity of the periodontal tissue-decomposing enzyme for periodontal tissues and on promoting the collagen synthesis, and have completed the present invention.

It is therefore an object of the present invention to provide a composition for preventing or treating periodontal diseases comprising at least one of extracts of (*Achyranthis radix, Ulmus cortex* and a mixture thereof as an active component.

Further objects and advantages of the invention will become apparent through reading the remainder of the specification.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a more thorough understanding of the invention may be had by referring to the detailed description of the preferred embodiment in addition to the scope of the invention defined by the claims.

DETAILED DESCRIPTION OF THE INVENTION

According to the present invention, a composition for preventing or treating periodontal diseases comprising at least one of extracts of *Achyranthis radix, Ulmus cortex* and a mixture thereof as an active component.

The active component of the composition according to the present invention is prepared from medicinal herbs, *Achyranthis radix* and *Ulmus cortex*.

*Achyranthis radix* which is one of the active components according to the present invention is distributed over the entire region of Korea, Japan and the south region of the Yellow River of China. The extract of *Achyranthis radix* is prepared from the root of *Achyranthis japonica* (This plant is otherwise called as *Achyranthes fauriei* or *Achyranthes bidentata*) which belongs to Amarantaceae family by eliminating the rootlets and drying the resulting root under the sunlight. It has a rod-shape or slightly bended cylindrical configuration of a length of 15 to 90 cm, and a diameter of 3 to 7 cm and contains a number of vertical wrinkles. Its color is a grayish yellow or a yellowish brown. In addition, scars of its lateral roots appear in many spots. The bended side of the root is flat and has a grayish white or a pale brown colour. Its central xylem has a yellowish white color. The contents of the xylem are solid, but fragile. It has little odor and is sticky. The taste is somewhat sweet. Microscopic observation of the cross section of it reveals that the xylem and the cortex are clearly discriminated by the cambia. A small primary xylem appears in the center of the xylem and parenchymatous cells contain quanterities of calcium hydroxide, but no starch granule is found. There has been known that it has pharmacological actions on diuresis, hemagogue, rheumathrithis, etc. The major components are composed of saponin, oleanolic glycoside, an insect modification hormone (e.g., inokosterone, or ecdysterone), betaine hydrate, etc.

*Ulmus cortex* which is another active medicinal herb component of the compositions according to the present invention and is prepared from the *Radicis cortex* of the stems or the roots of plants, Ulmaceae family such as *Ulmus macrocarpa, Ulmus pumila, Ulmus americana, Ulmus davidiana*, etc. by taking the necessary parts and drying the resulting roots under the sunlight. These are distributed over the northern region of Korea, Japan, China and America and are belong to Ulmaceae family. It has been known to have pharmacological actions on hydragogue, tumor, pain alleviation, dropsy, erysipelas inhibition. The major component includes β-sistosterol, plant sterol, tannin, etc. The term "*Ulmus cortex*" is otherwise called as *Ulmus radicis cortex*, but *Ulmus cortex* is more frequently called.

The present invention provides a dentifrice composition or an ointment composition for preventing or treating periodontal diseases comprising an extract of *Achyranthis radix, Ulmus cortex* or a mixture thereof. The composition is prepared as set forth below in detail.

In the preparation of the extracts of *Achyranthis radix* and *Ulmus cortex* according to the present invention, water or alcohols is used as an extraction solvent. The extracts of *Achyranthis radix* and *Ulmus cortex* used in the present invention, are first dried under the shade, segmented into small pieces and powdered. The resulting products are then extracted with water or alcohols, and filtered. The filtrate is concentrated under the reduced pressure to give each active component.

An alcoholic extraction solvent which can be used in the extraction step of *Achyranthis radix* or *Ulmus cortex* includes a lower $C_1$ to $C_4$ alcoholic solvent such as methanol, ethanol, propanol, butanol, etc, with ethanol being preferred.

The medicinal herb extracts according to the present invention are formulated into a dentifrice or an ointment composition in order to prevent or treat the periodontal diseases. The extract of *Achyranthis radix* or *Ulmus cortex* in each of the compositions according to the present invention is contained in an amount of 0.001 to 5% by weight based on the total weight of the composition, with 0.001 to 3% by weight being preferable. It is preferred that the same mixing ratio is applied to the mixture of the extracts of *Achyranthis radix* and *Ulmus cortex*. However, when the two medicinal herb extracts are combined, the mixed contents of 0.002 to 10% by weight based on the total weight of the composition are preferable. If each of the extracts is less than 0.001% by weight, it cannot expect the desirable therapeutic effects for the periodontal diseases. If each extract exceeds 5% by weight, it is inadequate because the stability of the products is lowered.

The dentifrice composition according to the present invention may further contain additives such as an abrasive, fluoride compound, a wetting agent, a binder, a foaming agent, and a sweetener.

The abrasive includes, but not limited thereto, one or more component selected from the group consisting of calcium monohydrogen phosphate, precipitated silica, silica gel, baking sodium carbonate, calcium carbonate, hydrated alumina, insoluble sodium metaphosphate, and sodium pyrophosphate. The abrasive component may typically used in an amount of 1 to 90% by weight of the composition, however, calcium monohydrogen phosphate, precipitated silica, and calcium carbonate alone or in combination are used in amount of 20 to 60% by weight in the preferred embodiment of the present invention.

Fluoride compound which is an active component for the recalcification of the teeth to reinforce the dental tissues includes one or more compound selected from the group consisting of sodium fluoride, sodium fluorophospliate and a mixture thereof, and it is preferred that the content thereof is in an amount of 0.01 to 2.0% by weight based on the total amount of the dentifrice composition. If the amount of the active component is below 0.01% by weight, it cannot expect a sufficient therapeutic effect for the periodontal diseases. If the amount of the active component exceeds 2.0% by weight, it is inadequate as a preparation for oral cavity because such an amount may affect a bad influence on the safety of the human body.

In order to maintain the configuration of the composition and to prevent drying of the composition, a wetting agent selected from the group consisting of glycerine, sorbitol solution, polyethylene glycol and propylene glycol alone or in combination is used in amount of 20 to 60% by weight of the composition.

A binder is used in order to bind an aqueous component and a solid component of the dentifrice composition to maintain the configuration of the dentifrice compositions and to secure the safety of the dentifrice composition. Such a binder mainly includes a natural or synthetic polymer such as sodium or calcium carrageenate (e.g., Carrageenan), sodium carboxymethyl cellulose, xanthan gum, acacia gum, etc. The contents thereof range from 0.1 to 5% by weight based on the total composition.

A foaming agent is used in order to assist the cleaning function of the abrasive agent and also has roles that it makes the active components to arrive at a region where a tooth brush cannot reach and increase the tooth feeling. Furthermore, it assists the cleaning function and promotes the dispersion and penetration of the active components and reduces the surface tension, thereby making foreign materials to be detached easily. An anionic surfactant such as sodium lauryl sulfate, sodium alkyl sulfate is used as the foaming agent. Non-ionic surfactant such as polyoxyethylene-polyoxypropylene copolymer, polyoxyethylene hardened caster oil, polyoxyethylene sorbitan fatty acid, alkanol amide fatty acid esters, sucrose fatty acid esters and polyoxyethylene caster oil are used supplementally. It is preferred that a 0.5 to 5% by weight of each of the non-ionic surfactants alone or in combination may be used.

In addition, a flavor or a sweetener can be added to the composition in order to compensate thick and tasteless or some bitter taste. As the flavor, a natural flavor such as peppermint or spearmint oil is commonly used. It is used in an amount of 0.1 to 1% by weight based on the dentifrice composition. As the sweetener, a synthetic or natural non-fermentative sucrose, etc. are mainly used, a typical example of which includes saccharine sodium, aspartame, lactose, maltose, xylitol, etc. It is preferable that the saccharine as the sweetener is used in an amount of 0.05 to 1% by weight based on the dentifrice composition.

As a buffer to adjust pH of the dentifrice composition, alkaline metal salts of orthophosphate, especially sodium dihydrogen phosphate, disodium hydrogen phosphate, sodium phosphate, citric acid, sodium citrate, phosphoric acid, hydrochloric acid, sodium hydroxide and sodium pyrophosphate, pyrophosphate, etc. In the preferred embodiment of the dentifrice compositions of the present invention, two components selected from the group consisting of sodium dihydrogen phosphate, disodium hydrogen phosphate, and sodium phosphate are suitably combined, the pH of which is adjusted to 5 to 8.

In order to prevent possible contaminations by a microbe during the preparation and use of the dentifrice composition, a further additive such as methyl paraoxybenzoate, benzoic acid, sodium benzoate, salicylic acid, etc. which are generally admitted to use in foodstuffs or medicines is added to the composition as alone or in combination of two or more in an amount of 0.01 to 0.5% by weight based on the dentifrice composition. When the extracts of *Achyranthis radix* and *Ulmus cortex* used in combination, the mixed contents of 0.002 to 10% by weight based on the dentifrice composition are preferable.

The present invention also provides an ointment composition comprising the extract of *Achyranthis radix, Ulmus cortex* or the mixture thereof. The composition is prepared as set forth above in detail.

The ointment composition according to the present invention may further contain one or more additive such as a conventionally used surfactant which stabilizes the status of the ointment composition, a solubilizing agent, a wetting agent, an active component delivery agent for oral soft tissues, a buffer, a preservative, a flavor or a sweetener.

As a surfactant for stabilizing the state of the ointment composition of the present invention, typically polyoxyethylene-polypropylene copolymer is used, an example of which includes Pluronic derivatives such as Pluronic F-127® or Pluronic F-108®. Such a surfactant in the ointment composition of the present invention may be used in an amount of 5 to 30% by weight based on the total weight of the composition.

As a solubilizing agent for the extracts of *Achyranthis radix* and *Ulmus cortex* according to the present invention, a lower $C_1$ to $C_4$ alcoholic solvent my be used. Example of the lower alcoholic solvent used for this purpose includes methanol, ethanol, isopropanol, butanol, etc. It is possible to use two or more alcohols in combination. It is preferable that the lower alcoholic solvent is used in an amount of 1 to 20% by weight based on the total weight of the ointment composition of the present invention.

A wetting agent may also be used in the ointment composition of the present invention in order to maintain the configuration and prevent drying of the ointment composition. Such an wetting agent includes one or more component selected from the group consisting of glycerine, sorbitol solution, polyethyleneglycol such as Plolyethyleneglycol 200, Polyethyleneglycol 400, Polyethyleneglycol 600, Polyethyleneglycol 1000, propylene glycol, Poloxamer 407 and monoglyceride (e.g., Myverol 18-99), and a mixture of two or more components. It is preferable that such a wetting agent is used in an amount of 5 to 40% by weight based on the total weight of the ointment composition of the present invention.

Meantime, as an active component delivery agent for delivering the active components of the composition by attaching them to the oral soft tissues, gelatin or pectin may be used alone or in combination in an amount of 1 to 30% by weight based on the total weight of the ointment composition of the present invention.

As a buffer to adjust pH of the ointment composition, alkaline metal salts of orthophosphate, especially sodium dihydrogen phosphate, disodium hydrogen phosphate, sodium phosphate, citric acid, sodium citrate, phosphoric acid, hydrochloric acid, sodium hydroxide, sodium pyrophosphate, pyrophosphate, etc. In the preferred embodiment of the ointment compositions of the present invention, one or two component selected from the group consisting of sodium dihydrogen phosphate, disodium hydrogen phosphate, sodium phosphate are suitably combined, the pH of which is adjusted to 5 to 8.

In addition, considering that the composition according to the present invention is applied to the oral cavity, a flavor or a sweetener may be added to the composition in order to compensate thick and tasteless or some bitter taste. As a flavor, a natural flavor such as peppermint or spearmint oil is commonly used. It is used in an amount of 0.1 to 1% by weight based on the total ointment composition. As the sweetener, a synthetic or natural non-fermentative sucrose, etc. are mainly used, a typical example of which includes saccharine sodium, aspartame, lactose, maltose, xylitol, etc. It is preferable that the saccharine as the sweetener is used in an amount of 0.05 to 1% by weight based on the dentifrice composition.

In order to prevent possible contaminations by a microbe during the preparation and use of the ointment composition according to the present invention, a further additive such as methyl paraoxybenzoate, benzoic acid, sodium benzoate, salicylic acid, etc. which are generally admitted to use in foodstuffs or medicines are added to the composition as alone or in combination of two or more components in an amount of 0.01 to 0.5% by weight based on the total ointment composition. When the extracts of *Achyranthis radix* and *Ulmus cortex* is used in combination, the mixed contents of 0.002 to 10% by weight based on the total ointment composition are preferable.

When the ointment composition of the present invention is clinically used, it is preferable that the composition mixed as discussed above is applied to the desired part in an amount of 50 to 500 mg, preferably 100 to 300 mg; however, this amount depends on the various factors such as the severity of the periodontal diseases, the size of the illness part, etc.

DESCRIPTION OF THE PREFERRED EMBODIMENTS

The present invention will be illustrated in greater detail by way of the following examples. The examples are presented for illustrative purpose only and should not be construed as limiting the invention, which is properly delineated in the claims.

PREPARATIVE EXAMPLE 1

50 mg of powder obtained by drying *Achyranthis radix* and then pulverizing was added into 500 ml of a 95% ethanol and precipitation-extracted for 3 days. The resulting solution was filtered with a paper of Whatman No. 1. The filtrate was then concentrated under the reduced pressure and dried to give 15 mg of an extract of *Achyranthis radix*.

PREPARATIVE EXAMPLE 2

50 mg of powder obtained by drying *Ulmus cortex* and then pulverizing was added into 500 ml of a 95% ethanol and precipitation-extracted for 3 days. The resulting solution was filtered with a paper of Whatman No. 1. The filtrate was then concentrated under the reduced pressure and dried to give 20 mg of an extract of *Ulmus cortex*.

EXAMPLES 1 TO 18 AND COMPARATIVE EXAMPLES 1 TO 18

The dentifrice compositions according to Examples 1 to 18 and Comparative Examples 1 to 18 were prepared based on the component ratio set forth in Tables 1 to 9 below.

TABLE 1

The component ratio of the dentifrice compositions (unit: % by weight)

| Additive | Component | Example 1-1 | Example 1-2 | Comparative Example 1-1 | Comparative Example 1-2 |
|---|---|---|---|---|---|
| Wetting agent | Glycerin | 20 | | 20 | |
| | Amorphous sorbitol solution | | 23 | | 23 |
| Binder | Carrageenan | 0.8 | | 0.8 | |
| | Carboxymethylcellulose | | 1 | | 1 |
| Surfactant | Sodium lauryl sulfate | 1 | 2 | 1 | 2 |
| | Sorbitan monooleate | 0.2 | 0.4 | 0.2 | 0.4 |
| Abrasive | Calcium monohydrogen phosphate | | 40 | | 40 |
| | Precipitated silica | 25 | | 25 | |
| | Calcium carbonate | — | — | — | — |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 0.001 | | | |
| | *Ulmus cortex* extract | | 0.001 | | |
| | Sodium fluoride | 0.22 | | 0.22 | |
| | Disodium fluorophosphate | | 0.76 | | 0.76 |
| Flavor | | 0.75 | 0.6 | 0.75 | 0.6 |
| Edible pigment | | 0.00025 | | 0.00025 | |
| Purified water up to | | 100 | 100 | 100 | 100 |

TABLE 2

The component ratio of the dentifrice compositions (unit: % by weight)

| Additive | Component | Example 1-3 | Example 1-4 | Comparative Example 1-3 | Comparative Example 1-4 |
|---|---|---|---|---|---|
| Wetting agent | Glycerin | 20 | | 20 | |
| | Amorphous sorbital solution | | 23 | | 23 |
| Binder | Carrageenan | 0.8 | | 0.8 | |
| | Carboxymethylcellulose | | 1 | | 1 |
| Surfactant | Sodium lauryl sulfate | 1 | 2 | 1 | 2 |
| | Sorbitan monooleate | 0.2 | 0.4 | 0.2 | 0.4 |
| Abrasive | Calcium monohydrogen phosphate | 40 | | 40 | |
| | Precipitated silica | | 25 | | 25 |
| | Calcium carbonate | — | — | — | — |
| Sweetener | Saccharine sodium | 0.1 | 0.2 | 0.1 | 0.2 |

TABLE 2-continued

The component ratio of the dentifrice compositions (unit: % by weight)

| Additive | Component | Example 1-3 | Example 1-4 | Comparative Example 1-3 | Comparative Example 1-4 |
|---|---|---|---|---|---|
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 0.01 | | | |
| | *Ulmus cortex* extract | | 0.01 | | |
| | Sodium fluoride | | 0.22 | | 0.22 |
| | Disodium fluorophosphate | 0.76 | | 0.76 | |
| Flavor | | 0.75 | 0.6 | 0.75 | 0.6 |
| Edible pigment | | 0.00025 | | 0.00025 | |
| Purified water up to | | 100 | 100 | 100 | 100 |

TABLE 3

The component ratio of the dentifrice compositions (unit: % by weight)

| Additive | Component | Example 1-5 | Example 1-6 | Comparative Example 1-5 | Comparative Example 1-6 |
|---|---|---|---|---|---|
| Wetting agent | Glycerin | 20 | | 20 | |
| | Amorphous sorbitol solution | | 23 | | 23 |
| Binder | Carrageenan | 0.8 | | 0.8 | |
| | Carboxymethyl-cellulose | | 1 | | 1 |
| Surfactant | Sodium lauryl sulfate | 1 | 2 | 1 | 2 |
| | Sorbitan monooleate | 0.2 | 0.4 | 0.2 | 0.4 |
| Abrasive | Calcium monohydrogen phosphate | 40 | | 40 | |
| | Precipitated silica | | 25 | | 25 |
| | Calcium carbonate | — | — | — | — |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 0.1 | | | |
| | *Ulmus cortex* extract | | 0.1 | | |
| | Sodium fluoride | | 0.22 | | 0.22 |
| | Disodium fluorophosphate | 0.76 | | 0.76 | |
| Flavor | | 0.75 | 0.6 | 0.75 | 0.6 |
| Edible pigment | | 0.00025 | | 0.00025 | |
| Purified water up to | | 100 | 100 | 100 | 100 |

TABLE 4

The component ratio of the dentifrice compositions (Unit: % by weight)

| Additive | Component | Example 1-7 | Example 1-8 | Comparative Example 1-7 | Comparative Example 1-8 |
|---|---|---|---|---|---|
| Wetting agent | Glycerin | 20 | | 20 | |
| | Amorphous sorbitol solution | | 23 | | 23 |
| Binder | Carrageenan | 0.8 | | 0.8 | |
| | Carboxymethyl-cellulose | | 1 | | 1 |
| Surfactant | Sodium lauryl sulfate | 1 | 2 | 1 | 2 |
| | Sorbitan monooleate | 0.2 | 0.4 | 0.2 | 0.4 |
| Abrasive | Calcium monohydrogen phosphate | 40 | | 40 | |
| | Precipitated silica | | 25 | | 25 |
| | Calcium carbonate | — | — | — | — |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 1 | | | |
| | *Ulmus cortex* extract | | 1 | | |
| | Sodium fluoride | | 0.22 | | 0.22 |
| | Disodium fluorophosphate | 0.76 | | 0.76 | |
| Flavor | | 0.75 | 0.6 | 0.75 | 0.6 |
| Edible pigment | | 0.00025 | | 0.00025 | |
| Purified water up to | | 100 | 100 | 100 | 100 |

TABLE 5

The component ratio of the dentifrice compositions (Unit: % by weight)

| Additive | Component | Example 1-9 | Example 1-10 | Comparative Example 1-9 | Comparative Example 1-10 |
|---|---|---|---|---|---|
| Wetting agent | Glycerin | 20 | | 20 | |
| | Amorphous sorbitol solution | | 23 | | 23 |
| Binder | Carrageenan | 0.8 | | 0.8 | |
| | Carboxymethyl-cellulose | | 1 | | 1 |
| Surfactant | Sodium lauryl sulfate | 1 | 2 | 1 | 2 |
| | Sorbitan monooleate | 0.2 | 0.4 | 0.2 | 0.4 |
| Abrasive | Calcium monohydrogen phosphate | 40 | | 40 | |
| | Precipitated silica | | 25 | | 25 |
| | Calcium carbonate | — | — | — | — |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 2 | | | |
| | *Ulmus cortex* extract | | 2 | | |
| | Sodium fluoride | | 0.22 | | 0.22 |
| | Disodium fluorophosphate | 0.76 | | 0.76 | |
| Flavor | | 0.75 | 0.6 | 0.75 | 0.6 |
| Edible pigment | | 0.00025 | | 0.00025 | |
| Purified water up to | | 100 | 100 | 100 | 100 |

TABLE 6

The component ratio of the dentifrice compositions (Unit: % by weight)

| Additive | Component | Example 1-11 | Example 1-12 | Comparative Example 1-11 | Comparative Example 1-12 |
|---|---|---|---|---|---|
| Wetting agent | Glycerin | 20 | | 20 | |
| | Amorphous sorbitol solution | | 23 | | 23 |
| Binder | Carrageenan | 0.8 | | 0.8 | |
| | Carboxymethyl-cellulose | | 1 | | 1 |
| Surfactant | Sodium lauryl sulfate | 1 | 2 | 1 | 2 |
| | Sorbitan monooleate | 0.2 | 0.4 | 0.2 | 0.4 |
| Abrasive | Calcium monohydrogen phosphate | 40 | | 40 | |
| | Precipitated silica | | 25 | | 25 |
| | Calcium carbonate | — | — | — | — |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 5 | | | |
| | *Ulmus cortex* extract | | 5 | | |
| | Sodium fluoride | | 0.22 | | 0.22 |
| | Disodium fluorophosphate | 0.76 | | 0.76 | |
| Flavor | | 0.75 | 0.6 | 0.75 | 0.6 |
| Edible pigment | | 0.00025 | | 0.00025 | |
| Purified water up to | | 100 | 100 | 100 | 100 |

TABLE 7

The component ratio of the dentifrice compositions (Unit: % by weight)

| Additive | Component | Example 1-13 | Example 1-14 | Comparative Example 1-13 | Comparative Example 1-14 |
|---|---|---|---|---|---|
| Wetting agent | Glycerin | 20 | | 20 | |
| | Amorphous sorbitol solution | | 23 | | 23 |
| Binder | Carrageenan | 0.8 | | 0.8 | |
| | Carboxymethyl-cellulose | | 1 | | 1 |
| Surfactant | Sodium lauryl sulfate | 1 | 2 | 1 | 2 |
| | Sorbitan monooleate | 0.2 | 0.4 | 02 | 0.4 |
| Abrasive | Calcium monohydrogen phosphate | | | | |
| | Precipitated silica | | 25 | | 25 |
| | Calcium carbonate | 38 | — | 38 | — |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 0.001 | 0.01 | | |
| | *Ulmus cortex* extract | 0.001 | 0.01 | | |
| | Sodium fluoride | | 0.22 | | 0.22 |
| | Disodium fluorophosphate | 0.76 | | 0.76 | |
| Flavor | | 0.75 | 0.6 | 0.75 | 0.6 |

TABLE 7-continued

The component ratio of the dentifrice compositions (Unit: % by weight)

| Additive | Component | Example 1-13 | Example 1-14 | Comparative Example 1-13 | Comparative Example 1-14 |
|---|---|---|---|---|---|
| Edible pigment | | 0.00025 | | 0.00025 | |
| Purified water up to | | 100 | 100 | 100 | 100 |

TABLE 8

The component ratio of the dentifrice compositions (Unit: % by weight)

| Additive | Component | Example 1-15 | Example 1-16 | Comparative Example 1-15 | Comparative Example 1-16 |
|---|---|---|---|---|---|
| Wetting agent | Glycerin | 20 | | 20 | |
| | Amorphous sorbitol solution | | 23 | | 23 |
| Binder | Carrageenan | 0.8 | | 0.8 | |
| | Carboxymethylcellulose | | 1 | | 1 |
| Surfactant | Sodium lauryl sulfate | 1 | 2 | 1 | 2 |
| | Sorbitan monooleate | 0.2 | 0.4 | 0.2 | 0.4 |
| Abrasive | Calcium monohydrogen phosphate | | 40 | | 40 |
| | Precipitated silica | 25 | | 25 | |
| | Calcium carbonate | — | — | — | — |
| Sweetener | Saccharine sodium | 0.1 | 0.2 | 0.1 | 0.2 |
| Buffer | Sodium dihydrogen phosphate | 0.1 | 1 | 0.1 | 1 |
| | Sodium phosphate | 0.1 | 1 | 0.1 | 1 |
| Active component | *Achyranthis radix* extract | 0.1 | 1 | | |
| | *Ulmus cortex* extract | 0.1 | 1 | | |
| | Sodium fluoride | 0.22 | | 0.22 | |
| | Disodium fluorophosphate | | 0.76 | | 0.76 |
| Flavor | | 0.75 | 0.6 | 0.75 | 0.6 |
| Edible pigment | | 0.00025 | | 0.00025 | |
| Purified water up to | | 100 | 100 | 100 | 100 |

TABLE 9

The component ratio of the dentifrice compositions (Unit: % by weight)

| Additive | Component | Example 1-17 | Example 1-18 | Comparative Example 1-17 | Comparative Example 1-18 |
|---|---|---|---|---|---|
| Wetting agent | Glycerin | 20 | | 20 | |
| | Amorphous sorbitol solution | 23 | | 23 | |
| Binder | Carrageenan | 0.8 | | 0.8 | |
| | Carboxymethylcellulose | | 1 | | 1 |
| Surfactant | Sodium lauryl sulfate | 1 | 2 | 1 | 2 |
| | Sorbitan monooleate | 0.2 | 0.4 | 0.2 | 0.4 |
| Abrasive | Calcium monohydrogen phosphate | | 40 | | 40 |
| | Precipitated silica | 25 | | 25 | |
| | Calcium carbonate | — | — | — | — |
| Sweetener | Saccharine sodium | 0.1 | 0.2 | 0.1 | 0.2 |
| Buffer | Sodium dihydrogen phosphate | 0.1 | 1 | 0.1 | 1 |
| | Sodium phosphate | 0.1 | 1 | 0.1 | 1 |
| Active component | *Achyranthis radix* extract | 2 | 5 | | |
| | *Ulmus cortex* extract | 2 | 5 | | |
| | Sodium fluoride | 0.22 | | 0.22 | |
| | Disodium fluorophosphate | | 0.76 | | 0.76 |
| Flavor | | 0.75 | 0.6 | 0.75 | 0.6 |
| Edible pigment | | 0.00025 | | 0.00025 | |
| Purified water up to | | 100 | 100 | 100 | 100 |

EXPERIMENTAL EXAMPLE 1-1

Inhibition Effects on the Superoxide Production of the Dentifrice Compositions according to the Present Invention 200 ml of venous blood taken from a healthy adult without any systemic diseases using citric acid as an anticoagulant was centrifuged for 10 minutes with 1200 rpm. Leucocyte concentrates were first collected from the middle phase, and then diluted with RPMI 1640 medium (Sigma R6504) at a 1:1 ratio. 30 ml of the diluted blood was carefully added to a 50 ml centrifuge tube filled with 12 ml of Ficoll-Paque to form a middle phase. After the tube was centrifuged for 30 minutes at 1600 rpm, a supernatant containing the sera was discarded and a middle phase containing mononuclear cells was carefully transferred to a fresh centrifuge tube with a sterilized pipet and then 3× of RPMI 1640 medium was added thereto. The mixture was centrifuged for 10 minutes at 800 rpm to discard the supernatant. 10 ml of RPMI 1640 medium was added to the resulting materials and gently pipetted with pipet aid. The tube was centrifuged for 10 minutes with 800 rpm to discard the supernatant and 25 ml of HBSS (Hank's balanced salt solution) buffer was added to the resulting mixture and pipetted with pipet aid. 0.45 ml of the human mononuclear leucocytes was pipetted into a 24-well plate to a concentration of $10^6$ cell/well. After the plate was aseptically cultivated for 2 hours under the condition of 95% air, 5% $CO_2$, 100% humidity, and the plate was treated with 0.05 ml of FMLP (N-formyl-Met-Leu-Phe) to a concentration of $10^{-6}$ M and incubated for 15 minutes at 37° C. to stimulate the cells. To this was added 0.1 ml of 80 μM Cytochrome C, 0.1 ml of 30 μg superoxide dismutase, 0.1 ml of the dentifrice compositions of the example and the comparative examples which were diluted with 3 times, and from which cytotoxic surfactants were excluded. The HBSS was supplemented to give 0.9 ml of the total reaction solution. The resulting solution was incubated for 10 minutes at 37° C. Then, 0.1 ml of a phagocytized Zymosan A which is a stimulating agent to a final concentration of 1.3 mg/ml were added thereto. After the resulting solution was incubated for 90 minutes at 37° C. with shaking, the reaction was stopped for 10 minutes at 4° C. and then centrifuged with 1500 rpm for 10 minutes at 4° C. Optical density at 550 nm was determined for the supernatant and the amount of superoxide anion production was calculated according to the following formulas:

$$O^{-2} = (\Delta O.D./21.0) \times 10^3 (nmols/10^6 \ cell.min)$$

$$\Delta O.D. = (B-D)-(A-C) = (B+C)-(D-A)$$

|  | A | B | C | D |
|---|---|---|---|---|
| Mononuclear leucocyte | 0.5 ml | 0.45 ml | 0.5 ml | 0.45 ml |
| Cytochrome C | 0.1 ml | 0.1 ml | 0.1 ml | 0.1 ml |
| SOD | — | — | 0.1 ml | 0.1 ml |
| FMLP | — | 0.05 ml | — | 0.05 ml |
| Zymosan | — | 0.1 ml | — | 0.1 ml |
| Test group | — | 0.1 ml | — | — |
| Reaction volume | 0.4 ml | 0.2 ml | 0.3 ml | 0.2 ml |
| Total volume | 1.0 ml | 1.0 ml | 1.0 ml | 1.0 ml |

The estimated results are represented at Table 10 below.

TABLE 10

| Dentifrice Composition | Amount of superoxide anion produced (unit: mmols.10$^6$ cell.min) | |
|---|---|---|
|  | Example | Comparative Example |
| 1-1 | 3.571 | 8.476 |
| 1-2 | 7.420 | 8.475 |
| 1-3 | 3.425 | 8.470 |
| 1-4 | 7.415 | 8.512 |
| 1-5 | 2.414 | 8.503 |
| 1-6 | 7.416 | 8.477 |
| 1-7 | 0.925 | 8.452 |
| 1-8 | 7.428 | 8.482 |
| 1-9 | 0.264 | 8.452 |
| 1-10 | 7.125 | 8.383 |
| 1-11 | 0.234 | 8.241 |
| 1-12 | 7.100 | 8.454 |
| 1-13 | 3.264 | 8.384 |
| 1-14 | 3.245 | 8.466 |
| 1-15 | 2.414 | 8.502 |
| 1-16 | 0.924 | 8.475 |
| 1-17 | 0.245 | 8.454 |
| 1-18 | 0.242 | 8.510 |

As can be seen from the test results in Table 10 above, the inhibition effects on the superoxide production have increased as the concentration of extract of *Achyranthis radix* increases in the compositions according to Examples 1-1, 5, 7, 9 and 11 which contain 0.001% by weight or more of the extract of *Achyranthis radix* while there was no inhibition effect on the superoxide production by the *Ulmus cortex* extract in the composition of Examples 1-2, 4, 6, 8, 10 and 12. The compositions of Examples 1-13, 14, 15, 16, 17, and 18 which have both the extracts of the *Achyranthis radix* and *Ulmus cortex* showed that the inhibition effects on the superoxide production have increased as the concentration of extract of *Achyranthis radix* increases.

EXPERIMENTAL EXAMPLE 1-2

Inhibition Effects of the Dentifrice Compositions According to the Present Invention on the Enzymatic Activity of Collagenase which is a Periodontal Tissue-decomposing Enzyme In this experiment, inhibition effects on the enzymatic activity of collagenase which is periodontal tissue-decomposing enzyme were tested with the dentifrice compositions according to the present invention. The experiment was carried out as follows:

The instant experimental procedures mimic the in vivo oral cavity environment wherein collagen which is a substrate for the periodontal tissues is decomposed by the action of the enzyme, collagenase contained in saliva and gingival crevice solutions of the patients suffering from the periodontal diseases which have been secreted from the periodontal disease-inducing bacteria or *Porhyromonas gingivalis* and *Polyrnorphonuclear leucocytes* and Neutrophil.

To each of 25 Eppendorf tubes (1.5 ml) was added 100 μl of 2% Azocol (Sigma) solution which is a substrate for red collagen. One of the tube was used as a blank. To the three tubes was added a collagenase Type I standard enzyme (available from Sigma, Inc.; lytic activity of 315 units/mg) to concentrations of 10, 100 and 200 ppm, respectively. To each of the remaining tubes was added 100 μl of collagenase purified from saliva and gingival crevice solutions of the patients suffering from the periodontal diseases through Sephacryl S-200 chromatography. One of the tubes was used as a control. In the meantime, each of the dentifrice compositions of the experimental group (Examples 1-1 to 1-18) and the comparative group (Comparative examples 1-1 to 1-18) from which cytotoxic surfactants were excluded was mixed with distilled water in a 1:2 ratio. The solutions were homogenized and centrifuged for 10 minutes at 5000×g. Each tube was treated with 10 μl of the resulting supernatant, respectively. A buffer solution (0.05 M Tris-HCl, 1 nM CaCl$_2$, pH 7.8) was added to give a total of 500 μl of the reaction solution. Then, after reacting for 18 hours in a 37° C. incubator, the Eppendorf tubes were centrifuged for 5 minutes at 10,000×g. The resulting undecomposed collagens were precipitated while the supernatant containing decomposed collagens were taken and determined absorbencies at 540 nm. From the obtained results, standard activity curve was plotted. Based on the standard curve, an activity concentration of the enzyme was calculated to compare the enzyme activities of the test group and the control group. The results are set forth in Table 11 below.

TABLE 11

| Dentifrice composition | Enzymatic activity (*unit: %) | |
|---|---|---|
|  | Example | Comparative Example |
| 1-1 | 98 | 98 |
| 1-2 | 97 | 98 |
| 1-3 | 77 | 97 |
| 1-4 | 75 | 95 |
| 1-5 | 66 | 98 |
| 1-6 | 65 | 98 |
| 1-7 | 25 | 97 |
| 1-8 | 27 | 97 |
| 1-9 | 12 | 100 |
| 1-10 | 9 | 98 |

TABLE 11-continued

Enzymatic activity
(*unit: %)

| Dentifrice composition | Example | Comparative Example |
|---|---|---|
| 1-11 | 0 | 97 |
| 1-12 | 0 | 96 |
| 1-13 | 84 | 97 |
| 1-14 | 65 | 100 |
| 1-15 | 43 | 98 |
| 1-16 | 7 | 98 |
| 1-17 | 0 | 97 |
| 1-18 | 0 | 97 |

*unit: % = (Enzymatic activity of the test group / enzymatic activity of the control group) × 100

As can be seen from Table 11 above, the inhibition effects against the collagenase activity have increased as the concentration of extracts of Achyranthis radix increases in the compositions of Examples 1-1, 5, 7, 9, and 11 which contain 0.01% by weight or more of the extract of Achyranthis radix. Also, the inhibition effects against the collagenase activity have increased as the concentration of extract of Ulmus cortex extracts increases in the compositions of Examples 1-2, 4, 6, 8, 10 and 12. It was confirmed that both the Achyranthis radix and Ulmus cortex show excellent inhibition effects against collagen activity. The results of the experiments on the compositions of Examples 1-13, 14, 15, 16, 17, and 18 which have both the extracts of the Achyranthis radix and Ulmus cortex showed a synergic effect.

EXPERIMENTAL EXAMPLE 1-3
Inhibition Effects of the Dentifrice Compositions According to the Present Invention on Interleukin (IL-1β) Production 0.8 ml of the mononuclear leucocyte isolated from human blood was added into a 24-well plate to a concentration of $10^6$ cell/well. A well containing 200 μl of RPMI 1640 medium was used as a control group. A well containing 100 μl of E. coli LPS (250 ppm) and wells containing 100 μl of E. coli LPS (250 ppm) and 100 μl of the diluted (3×) dentifrice compositions of Examples 1-1 to 1-18 and Comparative examples 1-1 to 1-18 from which cytotoxic surfactants were excluded were used as the experimental groups. After the plate was cultivated for 24 hours at 37° C., 50 μl of arachidonic acid was added and further cultivated for 30 minutes. To the wells of a 96-well palate that an antibody for interleukin (IL-1β) are conjugated, 50 μl of each standard solution (0, 10.24, 25.6, 64, 160, and 400 pg/well) was added, and then 50 ml of the above culture medium was added to the wells of the experimental groups. To all of the wells, 50 μl of biotinylated antibody reagent was added and the mixture was maintained for 30 minutes for 25° C. The resulting wells were washed with a washing buffer (a phosphate buffer containing 0.05% of Tween 20, pH 7.5), and then 50 μl of Streptavidine-HRP conjugate was added to all of the wells and again this was kept for 30 minutes at 25° C. The resulting wells were again washed 3 times with the washing buffer and thereafter 100 μl of the substrate for enzyme (3,3'5,5'-tetramethylbenzimidine/hydrogen peroxide) was added immediately and kept on dark room for 30 minutes while the cover of the plate was opened and added 100 μl of sulfuric acid (0.18M). Optical density at 450 nm was determined with a micro-plate detector (Bio-Tek instruments, EL340). Based on the absorbance of the standard solution, a standard activity curve was plotted. Then, the amount of interleukin production was calculated. The results are set forth in Table 12 below.

TABLE 12

Amount of IL-1β
(unit: pg)

| Dentifrice composition | Example | Comparative Example |
|---|---|---|
| Blank | 624 | 624 |
| Control | 1908 | 1908 |
| 1-1 | 1597 | 2196 |
| 1-2 | 1871 | 1881 |
| 1-3 | 881 | 1921 |
| 1-4 | 1721 | 1889 |
| 1-5 | 724 | 1787 |
| 1-6 | 1723 | 1854 |
| 1-7 | 638 | 1921 |
| 1-8 | 1734 | 1851 |
| 1-9 | 625 | 1907 |
| 1-10 | 1725 | 1903 |
| 1-11 | 624 | 1905 |
| 1-12 | 1721 | 1906 |
| 1-13 | 1582 | 1904 |
| 1-14 | 871 | 1987 |
| 1-15 | 723 | 1911 |
| 1-16 | 632 | 1924 |
| 1-17 | 624 | 1931 |
| 1-18 | 624 | 1905 |

As a result of the experiments on the efficacy and effects on human IL-1β stimulated with E. coli LPS, in the compositions according to Examples 1-3, 5, 7, 9 and 11 which contain 0.01% by weight or more of the extract of Achyranthis radix, the inhibition effects have increased as the concentration of extract of Achyranthis radix increases while there was no inhibition effect on the IL-1β production by the Ulmus cortex extract in the composition of Examples 1-2, 4, 6, 8, 10 and 12. The compositions of Examples 1-13, 14, 15, 16, 17, and 18 which contain both the extracts of the Achyranthis radix and Ulmus cortex showed that the inhibition effects of the superoxide production have increased as the concentration of extract of Achyranthis radix increases.

EXPERIMENTAL EXAMPLE 1-4
Inhibition Effects of the Dentifrice Compositions According to the Present Invention on Prostaglandin Production of Mononuclear Leukocyte This experiment was carried out to evaluate inhibition effects against the production of prostaglandin which is a periodontal disease-inducing agent with the dentifrice compositions according to the present invention. The detailed experimental procedures are as set forth below.

The instant experimental procedures use an immune diagnosis for antigen-antibody in determining the inhibition effects of the dentifrice compositions on the production of prostaglandin induced by stimulating human mononuclear leukocyte with lipopolysaccharide, a cell wall constituting component of Porhyromonas gingivalis which is periodontal disease-inducing bacteria in the development process of the periodontal diseases. The compositions of test group dentifrices (Examples 1-1 to 1-18) and comparative group dentifrices (Comparative Examples 1-1 to 1-18) from which cytotoxic surfactants were excluded were diluted with distilled water and homogenized throughly and centrifuged for 10 minutes at 5000×g and the supernatant was then discarded. The detailed experimental procedures are as set forth below.

To a blank well of a goat anti-mouse IgG conjugated 96-well plate, 50 μl of a buffer solution (0M phosphate buffer solution containing 0.9% NaCl, 0.1% bovine serum albumin, and 0.5% kathon) was added. To the standard well was added 50 μl of each standard solution (0, 2.5, 5, 10, 20, 40, 80, 160, and 320 pg/well). Thereafter, 50 μl of each of the test group dentifrice compositions (Examples 1-1 to 1-18) and Comparative group dentifrice compositions (Comparative Examples 1-1 to 1-18) from which cytotoxic surfactants were excluded and prepared as described above was added to the wells established as the test and control groups. 50 μl of PEG$_2$-conjugated peroxidase wherein 50 μl of an antibody against PEG$_2$ was added except for the blank well was added to all of the wells except for the blank well. The 96-well plate was covered and maintained for 1 hour at 25° C. Each well was washed with a washing buffer (a phosphate buffer containing 0.05% of Tween 20, pH 7.5) with four times, and thereafter 150 μl of the substrate for enzyme (3,3'5,5'-tetramethylbenzimidine/hydrogen peroxide) was added immediately and kept on for 30 minutes at 25° C. and added 100 μl of sulfuric acid (1 M). Absorbance at 450 nm was determined with a micro-plate detector (Bio-Tek instruments, EL340). Based on the absorbance of the standard solution, a standard activity curve was plotted to calculate the amount of prostaglandin production. The results are set forth in Table 13 below.

TABLE 13

| Dentifrice Composition | Amount of PGE$_2$ (unit: pg) | |
|---|---|---|
| | Example | Comparative Example |
| 1-1 | 194 | 250 |
| 1-2 | 245 | 254 |
| 1-3 | 154 | 232 |
| 1-4 | 232 | 238 |
| 1-5 | 112 | 245 |
| 1-6 | 231 | 250 |
| 1-7 | 74 | 246 |
| 1-8 | 225 | 247 |
| 1-9 | 57 | 239 |
| 1-10 | 224 | 251 |
| 1-11 | 56 | 242 |
| 1-12 | 234 | 248 |
| 1-13 | 192 | 238 |
| 1-14 | 145 | 239 |
| 1-15 | 110 | 242 |
| 1-16 | 75 | 245 |
| 1-17 | 56 | 246 |
| 1-18 | 55 | 254 |

As a result of the experiment on the efficacy and effects on the PGE$_2$ production by human mononuclear leukocyte stimulated with *E. coli* LPS, in the compositions according to Examples 1-3, 5, 7, 9 and 11 which contained 0.01% by weight or more of the *Achyranthis radix* extract, the inhibition effects have increased as the concentration of extract of *Achyranthis radix* increases while there was no inhibition effect on the PGE$_2$ production by the *Ulmus cortex* extract in the composition of Examples 1-2, 4, 6, 8, 10 and 12. The compositions of Examples 1-13, 14, 15, 16, 17, and 18 which have both the extracts of the *Achyranthis radix* and *Ulmus cortex* showed that the inhibition effects on the PGE$_2$ production have increased as the concentration of extract of *Achyranthis radix* increases.

EXPERIMENTAL EXAMPLE 1-5
Effects of the Dentifrice Compositions According to the Present Invention on Collagen Protein Production of Gingival Fibroblasts Gingival fibroblasts subjected to a primary culture were pipetted into a 24-well plate to a concentration 10$^6$ cell/well. After the fibroblast was cultivated in DMEM medium containing 10% FBS for one day, the preexisting medium was replaced with a fresh medium in the next day and the cultivation was continued for 24 hours. And then the cells attached to the bottom were washed with HBSS buffer solution and 0.8 ml of MEM medium which does not contain serum and proline was added thereto. The compositions of the test group dentifrices (Examples 1-1 to 1-18) and the comparative group dentifrices (Comparative Examples 1-1 to 1-18) from which cytotoxic surfactants were excluded were diluted with distilled water in a 1:2 ratio and homogenized throughly and centrifuged for 10 minutes at 5000×g and the supernatant was discarded. The cells were then cultivated in the medium containing 100 μl of $^{14}$C-proline (10 Ci). After 24 hours, the amounts of total proteins and collagen protein were determined. In order to first determine the amount of the total synthesized extracellular proteins, the culture media at each well were placed into a dialysis tube of which one end is sealed and then the other end was sealed. After dialysis was carried out for 24 hours in a cold buffer (Tris-HCl 0.05 mol/l, NaCl 0.2 mol/l, CaCl$_2$ 0.05 mol/l, phenylmethylsulfonyl fluoride 0.3 mN), each 100 μl was taken and put into a counting vial to which 10 ml of scintillation cocktail was added. Radioactivity was determined for 1 minute with a liquid scintillation counter (LSC). In order to determine the amount of the total synthesized intracellular proteins, 0.1 N NaOH and 0.5 mN phenyl methyl sulfonyl fluoride were added to each well that cell culture media was eliminated and then maintained for 30 minutes at 60° C. to lyse the cell walls. The culture media at each well were placed into a dialysis tube of which one end is sealed and then the other end was sealed. After dialysis was carried out for 24 hours in a cold buffer (Tris-HCl 0.05 mol/l, NaCl 0.2 mol/l, CaCl$_2$ 0.05 mol/l, phenylmethylsulfonyl fluoride 0.3 mN), each of 100 μl was taken and put into a counting vial to which 10 ml of scintillation cocktail was added. Radioactivity was determined for 1 minute with the liquid scintillation counter. In order to determine the amount the total synthesized intra- and intercellular collagen proteins, 100 μl of each of the cell culture media and cell homogenates that dialysis has been completed were taken and placed into a 1.5 ml microtube to which 100 μl of collgenase buffer (0.05 M Tris-HCl, 1 mM CaCl$_2$, 0.03 mM phenyl methyl sulfonyl fluoride), and 100 ppm collagenase enzyme were added. Then, the mixture was maintained for 3 hours at 37° C. to completely decompose collagen. In order to remove the proteins undecomposed, 500 μl of a solution containing 50% trichloroacetic acid and 1% tannic acid were added and then deposited for 30 minutes. The resulting mixture was then centrifuged for 5 minutes with 1000×g. 100 μl of the supernatant was taken and put into the counting vial to which 10 ml of scintillation cocktail was added. Radioactivity was determined for 1 minute with the liquid scintillation counter. The results are set forth in Table 14 below.

TABLE 14

| Dentifrice Composition | Radioactivity (unit: cpm/10$^6$ cells) | |
|---|---|---|
| | Example | Comparative Example |
| 1-1 | 2660 | 2650 |
| 1-2 | 3540 | 2640 |
| 1-3 | 2320 | 2650 |
| 1-4 | 4520 | 2640 |
| 1-5 | 2650 | 2630 |
| 1-6 | 4940 | 2630 |

TABLE 14-continued

| Dentifrice Composition | Radioactivity (unit: cpm/10⁶ cells) | |
|---|---|---|
| | Example | Comparative Example |
| 1-7 | 2650 | 2630 |
| 1-8 | 5240 | 2540 |
| 1-9 | 2420 | 2590 |
| 1-10 | 5250 | 2620 |
| 1-11 | 2120 | 2610 |
| 1-12 | 5250 | 2660 |
| 1-13 | 2100 | 2640 |
| 1-14 | 5260 | 2650 |
| 1-15 | 3540 | 2640 |
| 1-16 | 4530 | 2530 |
| 1-17 | 4950 | 2620 |
| 1-18 | 5230 | 2630 |

In order to determine the efficacy and effects of the compositions on collagen production by human fibroblast, the dentifrice compositions according to the present invention were treated with the cell culture media containing $^{14}$C-proline. As a result, it was revealed that the collagen synthesis promotion effect was increased as the concentration of extract of *Ulmus cortex* increases in the compositions of Examples 1-2, 4 6, 8, 10 and 12 containing the extract of *Ulmus cortex* while there was no effect on the collagen synthesis promotion by the *Achyranthis radix* extract in the compositions according to Examples 1-3, 5, 7, 9 and 11 which contain the extract of *Achyranthis radix*. The compositions of Examples 1-13, 14, 15, 16, 17, and 18 which have both the extracts of the *Achyranthis radix* and *Ulmus cortex* showed that the collagen synthesis promotion effect has increased as the concentration of the extract of *Ulmus cortex* increases.

EXPERIMENTAL EXAMPLE 1-6
Clinical Tests on the Efficacy and Effects of the Dentifrice Compositions According to the Present Invention The dentifrice compositions according to the present invention were subjected to clinical tests against periodontal diseases as follows:

The volunteers for this test were selected from the patients suffering periodontal diseases having a regular set of teeth without any dental loss. A precise medical examination for oral cavity was carried out for a total of 120 patients selected. The volunteers' age ranged from 30 to 50 year old. The volunteers were divided into two groups (60 volunteers/group) containing each 30 patients according to an interval of 10 year age and the distinction of sex. The clinical tests were carried out for determining the therapeutic effects of the test group dentifrices (Examples 1-1 to 1-18) and the comparative test group dentifrice (Comparative Examples 1-1 to 1-18) on the periodontal diseases.

The grouped volunteers were educated for the oral health and a correct use of toothbrush and then subjected dental brushing with identical toothbrushes. After the early gingivial index was scored for the volunteers, they were continuously provided with the test group dentifrices and the comparative test group dentifrices. A medical examination for oral cavity was carried out after one week, 1 month, 3 months and 6 months to score the gingival index. The gingivitis index was measured in a manner that periodontal probe is first inserted into gingival pockets and then the edge of each tooth was screened under the condition that any press is not imposed to each tooth. After 30 seconds, the status of bleeding was measured and scored based on the following criterion.

| Score | Contents |
|---|---|
| 0 | No bleeding |
| 1 | Spot bleeding |
| 2 | Linear bleeding |
| 3 | Triangle type bleeding at dental crevice portion |
| 4 | Overall gingival bleeding |

The results are set forth in Table 15 below.

TABLE 15

| Dentifrice composition | Early | | 1 week later | | 1 month later | | 3 month later | | 6 month later | |
|---|---|---|---|---|---|---|---|---|---|---|
| | Ex. | Comp. Ex. | Ex. | Comp. Ex. | Ex. | Comp. Ex. | Ex. | Comp. Ex. | Ex. | Comp. Ex. |
| 1-1 | 1.04 | 1.05 | 1.26 | 1.43 | 1.64 | 2.45 | 1.89 | 3.24 | 2.54 | 3.56 |
| 1-2 | 1.05 | 1.02 | 1.20 | 1.35 | 1.83 | 2.37 | 2.25 | 3.11 | 2.82 | 3.41 |
| 1-3 | 1.04 | 1.03 | 1.28 | 1.44 | 1.65 | 2.42 | 1.85 | 3.34 | 2.43 | 3.54 |
| 1-4 | 1.05 | 1.01 | 1.21 | 1.37 | 1.80 | 2.39 | 2.20 | 3.22 | 2.62 | 3.45 |
| 1-5 | 1.04 | 1.03 | 1.26 | 1.43 | 1.72 | 2.45 | 1.80 | 3.25 | 2.34 | 3.64 |
| 1-6 | 1.05 | 1.04 | 1.25 | 1.38 | 1.86 | 2.42 | 2.19 | 3.31 | 2.54 | 3.38 |
| 1-7 | 1.04 | 1.03 | 1.26 | 1.45 | 1.68 | 2.42 | 1.79 | 3.35 | 2.21 | 3.57 |
| 1-8 | 1.05 | 1.02 | 1.20 | 1.37 | 1.45 | 2.38 | 2.18 | 3.41 | 2.54 | 3.47 |
| 1-9 | 1.04 | 1.03 | 1.26 | 1.43 | 1.43 | 2.39 | 1.75 | 3.53 | 2.02 | 3.53 |
| 1-10 | 1.05 | 1.01 | 1.20 | 1.39 | 1.83 | 2.37 | 2.25 | 3.41 | 2.43 | 3.49 |
| 1-11 | 1.04 | 1.03 | 1.26 | 1.43 | 1.42 | 2.44 | 1.89 | 3.34 | 1.92 | 3.52 |
| 1-12 | 1.05 | 1.02 | 1.20 | 1.38 | 1.83 | 2.38 | 2.25 | 3.42 | 2.42 | 3.43 |
| 1-13 | 1.07 | 1.04 | 1.09 | 1.35 | 1.24 | 2.37 | 1.34 | 3.32 | 2.34 | 3.46 |
| 1-14 | 1.05 | 1.05 | 1.06 | 1.35 | 1.14 | 2.36 | 1.25 | 3.35 | 3.02 | 3.45 |
| 1-15 | 1.06 | 1.03 | 1.07 | 1.42 | 1.11 | 2.42 | 1.24 | 3.43 | 1.72 | 3.48 |
| 1-16 | 1.07 | 1.03 | 1.07 | 1.35 | 1.09 | 2.45 | 1.15 | 3.52 | 1.21 | 3.52 |
| 1-17 | 1.05 | 1.05 | 1.05 | 1.36 | 1.06 | 2.37 | 1.10 | 3.45 | 1.15 | 3.53 |
| 1-18 | 1.07 | 1.06 | 1.07 | 1.38 | 1.08 | 2.38 | 1.09 | 3.34 | 1.09 | 3.56 |

As can be seen from the above clinical tests, therapeutic effects on the periodontal diseases of the dentifrice compositions according to the present invention (Examples 1-1 to 1-18) containing the extract of *Achyranthis radix* which can inhibit the productions of IL-1β and prostaglandin which are inducers of the periodontal diseases and inhibit the enzyme activity of collagenase which inhibits the superoxide production and decomposes periodontal tissues or the *Ulmus cortex* extract which can promotes collagen synthesis and inhibits the enzymatic activity of collagenase were shown to be superior to those of the compositions according to the Comparative Examples 1-1 to 1-18 at the time lapse of from one week to six months. That is, the gingival index according to the compositions of Comparative Examples have continuously increased from 1 month later while the dentifrice compositions developed by the present invention have markedly inhibited the occurrence the periodontal diseases and thus lowered the gingival index even if time passed. The compositions of Examples 1-13, 14, 15, 16, 17, and 18 which contain both the extracts of the *Achyranthis radix* and *Ulmus cortex* showed a synergic effects on the inhibition of the periodontal diseases.

EXAMPLES 2-1 TO 2-18 AND COMPARATIVE EXAMPLES 2-1 TO 2-18

The ointment compositions according to Examples 2-1 to 2-18 and the comparative Examples 2-1 to 2-18 were prepared by dissolving each component into a buffer solution and gelling the solution based on the combination ratio set forth in Tables 16 to 24 below.

TABLE 16

The component ratio of the ointment compositions (Unit: % by weight)

| Additive | Component | Example 2-1 | Example 2-2 | Comparative Example 2-1 | Comparative Example 2-2 |
|---|---|---|---|---|---|
| Wetting agent | Glycerin | 5 | | 5 | |
| | Polyethyleneglycol | | 5 | | 5 |
| | Carboxymethylcellulose | | | | |
| | Poloxamer 407 | 0.1 | | 0.1 | |
| | Monoglyceride (Miverol 18-99) | 10 | 15 | 10 | 15 |
| Active component | Gelatin | 5 | 5 | 5 | 5 |
| | Pectin | 5 | 5 | 5 | 5 |
| delivery agent | | | | | |
| Surfactant | Pluronic F-127 | 20 | | 20 | |
| | Pluronic F-108 | | 20 | | 20 |
| Lower alcohol | Ethanol | 5 | | 5 | |
| | Isopropyl alcohol | | 5 | | 5 |
| Preservative | Methyl paraoxybenzoate | 0.1 | 0.1 | 0.1 | 0.1 |
| | Propyl paraoxybenzoate | 0.05 | 0.05 | 0.05 | 0.05 |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 0.001 | | | |
| | *Ulmus cortex* extract | | 0.001 | | |
| Flavor | | 0.75 | 0.75 | 0.75 | 0.75 |
| Edible pigment | | 0.0002 | | 0.0002 | |
| Purified water up to | | 100 | 100 | 100 | 100 |

TABLE 17

The component ratio of the ointment compositions
(Unit: % by weight)

| Additive | Component | Example 2-3 | Example 2-4 | Comparative Example 2-3 | Comparative Example 2-4 |
|---|---|---|---|---|---|
| Wetting agent | Glycerin | 10 | | 10 | |
| | Polyethyleneglycol | | 5 | | 5 |
| | Carboxymethylcellulose | 0.5 | 0.1 | 0.5 | 0.1 |
| | Poloxamer 407 | 10 | | 10 | |
| | Monoglyceride (Miberol 18-99) | | 20 | | 20 |
| Active component delivery agent | Gelatin | 3 | 2 | 3 | 2 |
| | Pectin | 3 | 2 | 3 | 2 |
| Surfactant | Pluronic F-127 | 15 | | 15 | |
| | Pluronic F-108 | | 15 | | 15 |
| Lower alcohol | Ethanol | 5 | | 5 | |
| | Isopropyl alcohol | | 5 | | 5 |
| Preservative | Methyl paraoxybenzoate | 0.1 | 0.1 | 0.1 | 0.1 |
| | Propyl paraoxybenzoate | 0.05 | 0.05 | 0.05 | 0.05 |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 0.01 | | | |
| | *Ulmus cortex* extract | | 0.01 | | |
| Flavor | | 0.75 | 0.75 | 0.75 | 0.75 |
| Edible pigment | | 0.0002 | | 0.0002 | |
| Purified water up to | | 100.00 | 100.00 | 100.00 | 100.00 |

TABLE 18

The component ratio of the ointment compositions
(Unit: % by weight)

| Additive | Component | Example 2-5 | Example 2-6 | Comparative Example 2-5 | Comparative Example 2-6 |
|---|---|---|---|---|---|
| Wetting agent | Glycerin | 15 | | 15 | |
| | Polyethyleneglycol | | 5 | | 5 |
| | Carboxymethylcellulose | 0.5 | | 0.5 | |
| | Poloxamer 407 | 5 | 1 | 5 | 1 |
| | Monoglyceride (Miberol 18-99) | | 5 | | 5 |
| Active component delivery agent | Gelatin | 1 | 10 | 1 | 10 |
| | Pectin | 1 | 5 | 1 | 5 |
| Surfactant | Pluronic F-127 | 10 | | 10 | |
| | Pluronic F-108 | | 10 | | 10 |
| Lower alcohol | Ethanol | 5 | | 5 | |
| | Isopropyl alcohol | | 5 | | 5 |
| Preservative | Methyl paraoxybenzoate | 0.1 | 0.1 | 0.1 | 0.1 |
| | Propyl paraoxybenzoate | 0.05 | 0.05 | 0.05 | 0.05 |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 0.1 | | | |
| | *Ulmus cortex* extract | | 0.1 | | |
| Flavor | | 0.75 | 0.75 | 0.75 | 0.75 |
| Edible pigment | | 0.0002 | | 0.0002 | |
| Purified water up to | | 100.00 | 100.00 | 100.00 | 100.00 |

TABLE 19

The component ratio of the ointment compositions
(Unit: % by weight)

| Additive | Component | Example 2-7 | Example 2-8 | Comparative Example 2-7 | Comparative Example 2-8 |
|---|---|---|---|---|---|
| Wetting agent | Glycerin | 20 | | 20 | |
| | Polyethyleneglycol | | 5 | | 5 |
| | Carboxymethylcellulose | | | | |
| | Poloxamer 407 | 10 | | 10 | |
| | Monoglyceride (Miberol 18-99) | | 20 | | 20 |
| Active component delivery agent | Gelatin | 5 | 20 | 5 | 20 |
| | Pectin | 5 | 5 | 5 | 5 |
| Surfactant | Pluronic F-127 | 5 | | 5 | |
| | Pluronic F-108 | | 5 | | 5 |
| Lower alcohol | Ethanol | 10 | | 10 | |
| | Isopropyl alcohol | | 10 | | 10 |
| Preservative | Methyl paraoxybenzoate | 0.1 | 0.1 | 0.1 | 0.1 |
| | Propyl paraoxybenzoate | 0.05 | 0.05 | 0.05 | 0.05 |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 1 | | | |
| | *Ulmus cortex* extract | | 1 | | |
| Flavor | | 0.75 | 0.75 | 0.75 | 0.75 |
| Edible pigment | | 0.0002 | | 0.0002 | |
| Purified water up to | | 100.00 | 100.00 | 100.00 | 100.00 |

TABLE 20

The component ratio of the ointment compositions
(Unit: % by weight)

| Additive | Component | Example 2-9 | Example 2-10 | Comparative Example 2-9 | Comparative Example 2-10 |
|---|---|---|---|---|---|
| Wetting agent | Glycerin | 10 | | 10 | |
| | Polyethyleneglycol | | 10 | | 10 |
| | Carboxymethylcellulose | | | | |
| | Poloxamer 407 | | | | |
| | Monoglyceride (Miberol 18-99) | | | | |
| Active component delivery agent | Gelatin | 10 | 10 | 10 | 10 |
| | Pectin | 10 | 10 | 10 | 10 |
| Surfactant | Pluronic F-127 | 15 | 15 | 15 | 15 |
| | Pluronic F-108 | 15 | 15 | 15 | 15 |
| Lower alcohol | Ethanol | 10 | | 10 | |
| | Isopropyl alcohol | | 10 | | 10 |
| Preservative | Methyl paraoxybenzoate | 0.1 | 0.1 | 0.1 | 0.1 |
| | Propyl paraoxybenzoate | 0.05 | 0.05 | 0.05 | 0.05 |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 2 | | | |
| | *Ulmus cortex* extract | | 2 | | |
| Flavor | | 0.75 | 0.75 | 0.75 | 0.75 |
| Edible pigment | | 0.0002 | | 0.0002 | |
| Purified water up to | | 100.00 | 100.00 | 100.00 | 100.00 |

TABLE 21

The component ratio of the ointment compositions
(Unit: % by weight)

| Additive | Component | Example 2-11 | Example 2-12 | Comparative Example 2-11 | Comparative Example 2-12 |
|---|---|---|---|---|---|
| Wetting agent | Glycerin | 10 | | 10 | |
| | Polyethyleneglycol | | 10 | | 10 |
| | Carboxymethylcellulose | | | | |
| | Poloxamer 407 | 20 | | 20 | |
| | Monoglyceride (Miberol 18-99) | | 20 | | 20 |
| Active component delivery agent | Gelatin | 2 | 2 | 2 | 2 |
| | Pectin | 3 | 3 | 3 | 3 |
| Surfactant | Pluronic F-127 | 10 | | 10 | |
| | Pluronic F-108 | | 10 | | 10 |
| Lower alcohol | Ethanol | 10 | | 10 | |
| | Isopropyl alcohol | | 10 | | 10 |
| Preservative | Methyl paraoxybenzoate | 0.1 | 0.1 | 0.1 | 0.1 |
| | Propyl paraoxybenzoate | 0.05 | 0.05 | 0.05 | 0.05 |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 5 | | | |
| | *Ulmus cortex* extract | | 5 | | |
| Flavor | | 0.75 | 0.75 | 0.75 | 0.75 |
| Edible pigment | | 0.0002 | | 0.0002 | |
| Purified water up to | | 100.00 | 100.00 | 100.00 | 100.00 |

TABLE 22

The component ratio of the ointment compositions
(Unit: % by weight)

| Additive | Component | Example 2-13 | Example 2-14 | Comparative Example 2-13 | Comparative Example 2-14 |
|---|---|---|---|---|---|
| Wetting agent | Glycerin | 5 | | 5 | |
| | Polyethyleneglycol | | | | |
| | Carboxymethylcellulose | 1 | | 1 | |
| | Poloxamer 407 | 15 | 20 | 15 | 20 |
| | Monoglyceride (Miberol 18-99) | | 20 | | 20 |
| Active component delivery agent | Gelatin | 5 | 5 | 5 | 5 |
| | Pectin | 5 | 5 | 5 | 5 |
| Surfactant | Pluronic F-127 | 10 | | 10 | |
| | Pluronic F-108 | | 10 | | 10 |
| Lower alcohol | Ethanol | 10 | | 10 | |
| | Isopropyl alcohol | | 10 | | 10 |
| Preservative | Methyl paraoxybenzoate | 0.1 | 0.1 | 0.1 | 0.1 |
| | Propyl paraoxybenzoate | 0.05 | 0.05 | 0.05 | 0.05 |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 0.001 | 0.01 | | |
| | *Ulmus cortex* extract | 0.001 | 0.01 | | |
| Flavor | | 0.75 | 0.75 | 0.75 | 0.75 |
| Edible pigment | | 0.0002 | | 0.0002 | |
| Purified water up to | | 100.00 | 100.00 | 100.00 | 100.00 |

TABLE 23

The component ratio of the ointment compositions
(Unit: % by weight)

| Additive | Component | Example 2-15 | Example 2-16 | Comparative Example 2-15 | Comparative Example 2-16 |
|---|---|---|---|---|---|
| Wetting agent | Glycerin | 10 | | 10 | |
| | Polyethyleneglycol | | 10 | | 10 |
| | Carboxymethylcellulose | | | | |
| | Poloxamer 407 | 15 | 15 | 15 | 15 |
| | Monoglyceride (Miberol 18-99) | | | | |
| Active component delivery agent | Gelatin | 2 | 2 | 2 | 2 |
| | Pectin | 2 | 2 | 2 | 2 |
| Surfactant | Pluronic F-127 | 15 | | 15 | |
| | Pluronic F-108 | | 15 | | 15 |
| Lower alcohol | Ethanol | 10 | | 10 | |
| | Isopropyl alcohol | | 10 | | 10 |
| Preservative | Methyl paraoxybenzoate | 0.1 | 0.1 | 0.1 | 0.1 |
| | Propyl paraoxybenzoate | 0.05 | 0.05 | 0.05 | 0.05 |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 0.01 | 1 | | |
| | *Ulmus cortex* extract | 0.05 | 1 | | |
| Flavor | | 0.75 | 0.75 | 0.75 | 0.75 |
| Edible pigment | | 0.0002 | | 0.0002 | |
| Purified water up to | | 100 | 100 | 100 | 100 |

TABLE 24

The component ratio of the ointment compositions
(Unit: % by weight)

| Additive | Component | Example 2-17 | Example 2-18 | Comparative Example 2-17 | Comparative Example 2-18 |
|---|---|---|---|---|---|
| Wetting agent | Glycerin | 15 | | 15 | |
| | Polyethyleneglycol | | 15 | | 15 |
| | Carboxymethylcellulose | | | | |
| | Poloxamer 407 | 10 | 10 | 10 | 10 |
| | Monoglyceride (Miberol 18-99) | | | | |
| Active component delivery agent | Gelatin | 5 | 5 | 5 | 5 |
| | Pectin | 5 | 5 | 5 | 5 |
| Surfactant | Pluronic F-127 | 10 | | 10 | |
| | Pluronic F-108 | | 10 | | 10 |
| Lower alcohol | Ethanol | 10 | | 10 | |
| | Isopropyl alcohol | | 10 | | 10 |
| Preservative | Methyl paraoxybenzoate | 0.1 | 0.1 | 0.1 | 0.1 |
| | Propyl paraoxybenzoate | 0.05 | 0.05 | 0.05 | 0.05 |
| Sweetener | Saccharine sodium | 0.1 | 0.2 | 0.1 | 0.2 |
| Buffer | Sodium dihydrogen phosphate | 0.1 | 0.2 | 0.1 | 0.2 |
| | Sodium phosphate | 0.05 | 0.05 | 0.05 | 0.05 |
| Active component | *Achyranthis radix* extract | 2 | 5 | | |
| | *Ulmus cortex* extract | 2 | 5 | | |
| Flavor | | 0.75 | 0.75 | 0.75 | 0.75 |
| Edible pigment | | 0.0002 | | 0.0002 | |
| Purified water up to | | 100.00 | 100.00 | 100.00 | 100.00 |

EXPERIMENTAL EXAMPLE 2-1

Inhibition Effects of the Ointment Composition According to the Present Invention on Superoxide Production In this experiment, inhibition effects on the production of superoxide which is a periodontal disease-inducing material were tested with the ointment compositions according to the present invention. The experiment was carried out as follows:

200 ml of venous blood taken from a healthy adult without any systemic diseases using citric acid as an anticoagulant was centrifuged for 10 minutes with 1200 rpm. Leucocyte concentrates were first collected from the middle phase, and then diluted with RPMI 1640 medium (Sigma R6504) at 1:1 ratio. 30 ml of the diluted blood was carefully added to a 50 ml centrifuge tube filled with 12 ml of Ficoll-Paque to form a middle phase. After the tube was centrifuged for 30 minutes at 1600 rpm, a supernatant containing the sera was discarded and a middle phase containing mononuclear cells was carefully transferred to a fresh centrifuge tube with a sterilized pipet and then 3× of RPMI 1640 medium was added thereto. The mixture was centrifuged for 10 minutes at 800 rpm to discard the supernatant. 10 ml of RPMI 1640 medium was added to the resulting materials and gently pipetted with pipet aid. The tube was centrifuged for 10 minutes at 800 rpm to discard the supernatant and 25 ml of HBSS (Hank's balanced salt solution) buffer was added to the resulting mixture and pipetted with pipet aid. 0.45 ml of the human mononuclear leucocytes was pipetted into a 24-well plate to a concentration of $10^6$ cell/well. After the plate was aseptically cultivated for 2 hours under the condition of 95% air, 5% $CO_2$, 100% humidity, and the plate was treated with 0.05 ml of FMLP (N-formyl-Met-Leu-Phe) to a concentration of $10^{-6}$ M and incubated for 15 minutes at 37° C. to stimulate the cells. To this was added 0.1 ml of 80 μM Cytochrome C, 0.1 ml of 30 μg superoxide dismutase, 0.1 ml of the ointment compositions of the example and the comparative examples which were diluted with 3 times, and from which cytotoxic surfactants were excluded. The HBSS was supplemented to give 0.9 ml of the total reaction solution. The resulting solution was incubated for 10 minutes at 37° C. Then, 0.1 ml of a phagocytized Zymosan A which is a stimulating agent to a final concentration of 1.3 mg/ml were added thereto. After the resulting solution was incubated for 90 minutes at 37° C. with shaking, the reaction was stopped for 10 minutes at 4° C. and then centrifuged with 1500 rpm for 10 minutes at 4° C. Optical density at 550 nm was determined for the supernatant and the amount of superoxide anion production was calculated according to the following formulas:

$$O^{-2} = (\Delta O.D./21.0) \times 10^3 (nmols/10^6 \text{ cell.min})$$

$$\Delta O.D. = (B-D)-(A-C) = (B+C)-(D+A)$$

|  | A | B | C | D |
|---|---|---|---|---|
| Mononuclear leucocyte | 0.5 ml | 0.45 ml | 0.5 ml | 0.45 ml |
| Cytochrome C | 0.1 ml | 0.1 ml | 0.1 ml | 0.1 ml |
| SOD | — | — | 0.1 ml | 0.1 ml |
| FMLP | — | 0.05 ml | — | 0.05 ml |
| Zymosan | — | 0.1 ml | — | 0.1 ml |
| Test group | | 0.1 ml | | |
| Reaction volume | 0.4 ml | 0.2 ml | 0.3 ml | 0.2 ml |
| Total Volume | 1.0 ml | 1.0 ml | 1.0 ml | 1.0 ml |

The estimated results are represented at Table 25 below.

TABLE 25

| | Amount of superoxide anion (unit: nmols/$10^6$ cell · min) | |
|---|---|---|
| Ointment Composition | Example | Comparative Example |
| 2-1 | 3.572 | 8.476 |
| 2-2 | 7.520 | 8.475 |
| 2-3 | 3.425 | 8.470 |
| 2-4 | 7.415 | 8.512 |
| 2-5 | 2.414 | 8.503 |
| 2-6 | 7.416 | 8.477 |
| 2-7 | 0.925 | 8.452 |
| 2-8 | 7.428 | 8.482 |
| 2-9 | 0.264 | 8.452 |
| 2-10 | 7.125 | 8.383 |
| 2-11 | 0.243 | 8.241 |
| 2-12 | 7.100 | 8.454 |
| 2-13 | 3.264 | 8.384 |
| 2-14 | 3.245 | 8.466 |
| 2-15 | 2.414 | 8.502 |
| 2-16 | 0.924 | 8.475 |
| 2-17 | 0.245 | 8.454 |
| 2-18 | 0.242 | 8.510 |

As can be seen from test results in Table 25 above, the inhibition effects on the superoxide production have increased as tile concentration of extract of *Achyranthis radix* increases in the compositions according to Examples 2-1, 5, 7, 9 and 11 which contain 0.001% by weight or more of the extract of *Achyranthis radix* while there was no inhibition effect on the superoxide production by the *Ulmus cortex* extract in the composition of Examples 2-2, 4, 6, 8, 10 and 12. The compositions of Examples 2-13, 14, 15, 16, 17, and 18 which have both the extracts of the *Achyranthis radix* and *Ulmus cortex* showed that the inhibition effects on the superoxide production have increased as the concentration of extract of *Achyranthis radix* increases.

EXPERIMENTAL EXAMPLE 2-2
Inhibition Effects of the Ointment Compositions According to the Present Invention on the Enzymatic Activity of Collagenase which is a Periodontal Tissue-Decomposing Enzyme In this experiment, inhibition effects on the enzymatic activity of collagenase which is periodontal tissue-decomposing enzyme were tested with the ointment compositions according to the present invention. The experiment was carried out as follows:

The instant experimental procedures mimic the in vivo oral cavity environment wherein collagen which is a substrate for the periodontal tissues is decomposed by the action of the enzyme, collagenase contained in saliva and gingival crevice solutions of the patients suffering from the periodontal diseases which have been secreted from the periodontal disease-inducing bacteria or *Porhyromonas gingivalis* and *Polymorphonuclear leucocytes* and Neutrophil.

To each of 25 Eppendorf tubes (1.5 ml) was added 100 μl of 2% Azocol (Sigma A9409) solution which is a substrate for red collagen. One of the tube was used as a blank. To the three tubes was added a collagenase Type I standard enzyme (available from Sigma, Inc.; lytic activity of 315 units/mg) to concentrations of 10, 100 and 200 ppm, respectively. To each of the remaining tubes was added 100 1 of collagenase purified from saliva and gingival crevice solutions of the patients suffering from the periodontal diseases through Sephacryl S-200 chromatography. One of the tubes was used as a control. In the meantime, each of the ointment compositions of the experimental group (Examples 2-1 to 2-18) and the comparative group (Comparative examples 2-1 to 2-18) from which cytotoxic surfactants were eliminated was mixed with distilled water in a 1:2 ratio. The solutions were homogenized and centrifuged for 10 minutes at 5000×g. Each tube was treated with 10 μl of the resulting supernatant, respectively. A buffer solution (0.05M Tris-HCl, 1 nM $CaCl_2$, pH 7.8) was added so as to give a total of 500 μl of the reaction solution. Then, after reacting for 18 hours in a 37° C. incubator, the Eppendorf tubes were centrifuged for 5 minutes at 10,000×g. The resulting undecomposed collagens were precipitated while the supernatant containing decomposed collagens were taken and determined absorbencies at 540 nm. From the obtained results, standard activity curve was plotted. Based on the standard curve, an activity concentration of the enzyme was calculated to compare the enzyme activities of the test group and the control group. The results are set forth in Table 26 below.

TABLE 26

| Ointment Composition | Enzymatic activity (*unit: %) | |
|---|---|---|
| | Example | Comparative Example |
| 2-1 | 98 | 98 |
| 2-2 | 97 | 94 |
| 2-3 | 63 | 93 |
| 2-4 | 69 | 95 |
| 2-5 | 54 | 96 |
| 2-6 | 55 | 95 |
| 2-7 | 23 | 97 |
| 2-8 | 19 | 94 |
| 2-9 | 11 | 95 |
| 2-10 | 8 | 95 |
| 2-11 | 0 | 95 |
| 2-12 | 0 | 96 |
| 2-13 | 92 | 97 |
| 2-14 | 54 | 99 |
| 2-15 | 38 | 98 |
| 2-16 | 5 | 96 |
| 2-17 | 0 | 97 |
| 2-18 | 0 | 97 |

*unit: % = Enzyme activity of the test group × 100 / Enzyme activity of the control group As can he seen from Table 26 above, the inhibition effects against the collagenase activity have increased as the concentration of extract of *Achyranthis radix* increases in the compositions of Examples 2-1, 5, 7, 9, and 11 which contain 0.001% by weight or more of the extract of *Achyranthis radix*. Also, the inhibition effects against the collagenase activity have increased as the concentration of extract of *Ulmus cortex* extracts increases in the compositions of Examples 2-2, 4, 6, 8, 10 and 12. It was confirmed that both the *Achyranthis radix* and *Ulmus cortex* show excellent inhibition effects against collagen activity. The results of the experiments on the compositions of Examples 2-13, 14, 15, 16, 17, and 18 which have both the extracts of the *Achyranthis radix* and *Ulmus cortex* showed a synergic effect.

EXPERIMENTAL EXAMPLE 2-3
Inhibition Effects of the Ointment Compositions according to the Present Invention on Interleukin (IL-1β) Production In this experiment, inhibition effects on the production of interleukin (IL-1β) which is periodontal disease inducing material were tested with the ointment compositions according to the present invention. The experiment was carried out as follows:

0.8 ml of the mononuclear leucocyte isolated from human blood was added into a 24-well plate to a concentration of $10^6$ cell/well. A well containing 200 μl of RPMI 1640 medium was used as a control group. A well containing 100 μl of *E. coli* LPS (250 ppm) and wells containing 100 μl of *E. coli* LPS (250 ppm) and 100 μl of the diluted (3×) ointment compositions of Examples 2-1 to 2-18 and Comparative examples 2-1 to 2-18 from which cytotoxic surfactants were excluded were used as the experimental groups. After the plate was cultivated for 24 hours at 37° C., 50 μl of arachidonic acid was added and further cultivated for 30 minutes. To the wells of a 96-well palate that an antibody for interleukin (IL-1β) are conjugated, 50 μl of each standard solution (0, 10.24, 25.6, 64, 160, and 400 pg/well) was added, and then 50 ml of the above culture medium was added to the wells of the experimental groups. To all of the wells, 50 μl of biotinylated antibody reagent was added and the mixture was maintained for 30 minutes for 25° C. The resulting wells were washed with a washing buffer (a phosphate buffer containing 0.05% of Tween 20, pH 7.5), and then 50 μl of Streptavidine-HRP conjugate was added to all of the wells and again this was kept for 30 minutes at 25° C. The resulting wells were again washed 3 times with the washing buffer and thereafter 100 μl of the substrate for enzyme (3,3'5,5'-tetramethylbenzimidine/hydrogen peroxide) was added immediately and kept on dark room for 30 minutes while the cover of the plate was opened and added 100 μl of sulfuric acid (0.18M). Optical density at 450 nm was determined with the micro-plate detector. Based on the absorbance of the standard solution, a standard activity curve was plotted. Then, the amount of interleukin production was calculated. The results are set forth in Table 27 below.

TABLE 27

| Ointment Composition | Amount of IL-1β (unit: pg) | |
|---|---|---|
| | Example | Comparative Example |
| Blank | 621 | 621 |
| Control | 2131 | 2131 |
| 2-1 | 1584 | 2042 |
| 2-2 | 1741 | 1941 |
| 2-3 | 865 | 1911 |
| 2-4 | 1724 | 1941 |
| 2-5 | 701 | 1921 |
| 2-6 | 1711 | 1945 |
| 2-7 | 624 | 1921 |
| 2-8 | 1725 | 1924 |
| 2-9 | 624 | 1915 |
| 2-10 | 1710 | 1924 |
| 2-11 | 624 | 1916 |
| 2-12 | 1715 | 1906 |
| 2-13 | 1672 | 1910 |
| 2-14 | 863 | 1924 |
| 2-15 | 715 | 1911 |
| 2-16 | 629 | 1924 |
| 2-17 | 624 | 1931 |
| 2-18 | 624 | 1911 |

As a result of the experiments on the efficacy and effects on human IL-1β simulated with *E. coli* LPS as set forth in Table 27, the inhibition effects have increased as the concentration of extract of *Achyranthis radix* increases in the compositions according to Examples 2-3, 5, 7, 9 and 11 which contain 0.01% by weight or more of the *Achyranthis radix* extract while there was no inhibition effect on the IL-1β production by the *Ulmus cortex* extract in the composition of Examples 2-2, 5 4, 6, 8, 10 and 12. The compositions of Examples 2-13, 14, 15, 16, 17, and 18 which contained both the extracts of the *Achyranthis radix* and *Ulmus cortex* showed that the inhibition effects of the superoxide production have increased as the concentration of extract of *Achyranthis radix* increases.

EXPERIMENTAL EXAMPLE 2-4
Inhibition Effects of the Ointment Compositions according to the Present Invention on Prostaglandin Production of Mononuclear Leukocyte This experiment was carried out in order to evaluate the inhibition effects against the production of prostaglandin which is a periodontal disease-inducing agent with the ointment compositions according to the present invention. The detailed experimental procedures are as set forth below.

The instant experimental procedures use an immune diagnosis for antigen-antibody in determining the inhibition effects of the ointment compositions on the production of prostaglandin induced by stimulating human mononuclear leukocytes with lipopolysaccharide, a cell wall constituting component of *Porhyromonas gingivalis* which is periodontal disease-inducing bacteria in the development process of the periodontal diseases. The compositions of test group ointments (Examples 2-1 to 2-18) and comparative group ointments (Comparative Examples 2-1 to 2-18) from which cytotoxic surfactants were excluded were diluted with distilled water and homogenized throughly and centrifuged for 10 minutes at 5000×g and the supernatant was then discarded. The detailed experimental procedures are as set forth below.

To a blank well of a goat anti-mouse IgG conjugated 96-well plate, 50 μl of a buffer solution (0.1M phosphate buffer solution containing 0.9% NaCl, 0.1% bovine serum albumin, and 0.5% kathon was added. To the standard well was added 50 μl of each standard solution (0, 2.5, 5, 10, 20, 40, 80, 160, and 320 pg/well). Thereafter, 50 μl of each of the test group ointment compositions (Examples 2-1 to 2-18) and Comparative group ointment compositions (Comparative Examples 2-1 to 2-18) from which cytotoxic surfactants were excluded and prepared as described above was added to the wells established as the test and control groups. 50 μl of $PEG_2$-conjugated peroxidase wherein 50 μl of an antibody against $PEG_2$ was added except for the blank well was added to all of the wells except for the blank well. The 96-well plate was covered and maintained for 1 hour at 25° C. Each well was washed with a washing buffer (a phosphate buffer containing 0.05% of Tween 20, pH 7.5) with four times, and thereafter 150 μl of the substrate for enzyme (3,3'5,5'-tetramethylbenzimidine/hydrogen peroxide) was added immediately and kept on for 30 minutes at 25° C. and added 100 μl of sulfuric acid (1 M). Absorbance at 450 nm was determined with the micro-plate detector. Based on the absorbance of the standard solution, a standard activity curve was plotted to calculate the amount of prostaglandin production. The results are set forth in Table 28 below.

TABLE 28

| Ointment Composition | Amount of $PEG_2$ (unit: pg) | |
|---|---|---|
| | Example | Comparative Example |
| 2-1 | 184 | 243 |
| 2-2 | 234 | 242 |
| 2-3 | 142 | 243 |
| 2-4 | 223 | 238 |
| 2-5 | 109 | 240 |
| 2-6 | 225 | 241 |

TABLE 28-continued

| Ointment Composition | Amount of $PEG_2$ (unit: pg) | |
|---|---|---|
| | Example | Comparative Example |
| 2-7 | 76 | 246 |
| 2-8 | 227 | 247 |
| 2-9 | 58 | 239 |
| 2-10 | 226 | 248 |
| 2-11 | 55 | 225 |
| 2-12 | 225 | 248 |
| 2-13 | 182 | 238 |
| 2-14 | 134 | 230 |
| 2-15 | 108 | 245 |
| 2-16 | 73 | 248 |
| 2-17 | 54 | 246 |
| 2-18 | 52 | 244 |

As can be seen from the experiment results of Table 28 on the efficacy and effects on the $PGE_2$ production by human mononuclear leukocyte stimulated with *E. coli* LPS, the inhibition effects have increased as the concentration of extract of *Achyranthis radix* increases in the compositions according to Examples 2-3, 5, 7, 9 and 11 which contained 0.01% by weight or more of the extract of *Achyranthis radix* while there was no inhibition effect on the $PGE_2$ production by the *Ulmus cortex* extract in the compositions of Examples 2-2, 4, 6, 8, 10 and 12. The compositions of Examples 2-13, 14, 15, 16, 17, and 18 which have both the extract of the *Achyranthis radix* and *Ulmus cortex* showed that the inhibition effects on the $PGE_2$ production have increased as the concentration of extract of *Achyranthis radix* increases.

EXPERIMENTAL EXAMPLE 2-5
Effects of the Ointment Compositions According to the Present Invention on Collagen Protein Production of Gingival Fibroblast In this experiment, the collagen protein production of gingival fibroblast was tested with the ointment compositions according to the present invention. The experiment was carried out as follows:

Gingival fibroblasts subjected to a primary culture were pipetted into a 24-well plate to a concentration $10^6$ cell/well. After the fibroblast was cultivated in DMEM medium containing 10% FBS for one day, the preexisting medium was replaced with a fresh medium in the next day and the cultivation was continued for 24 hours. And then the cells attached to the bottom were washed with HBSS solution and 0.8 ml of MEM medium which does not contain serum and proline was added thereto. The compositions of the test group ointments (Examples 2-1 to 2-18) and the comparative group ointments (Comparative Examples 2-1 to 2-18) from which cytotoxic surfactants were excluded were diluted with distilled water in a 1:2 ratio and homogenized throughly and centrifuged for 10 minutes at 5000×g and the supernatant was discarded. The cells were then cultivated in the medium containing 100 μl of $^{14}$C-proline (10 Ci). After 24 hours, the amounts of total proteins and collagen protein were determined. In order to first determine the amount of the total synthesized extracellular proteins, the culture media at each well were placed into a dialysis tube of which one end is sealed and then the other end was sealed. After dialysis was carried out for 24 hours in a cold buffer (Tris-HCl 0.05 mol/l, Nacl 0.2 mol/l, $CaCl_2$ 0.05 mol/l, phenylmethylsulfonyl fluoride 0.3 mN), each 100 μl was taken and put into a counting via to which 10 ml of scintillation cocktail was added. Radioactivity was determined for 1 minute with a liquid scintillation counter (LSC). In order to determine the amount of the total synthesized intracellular proteins, 0.1 N NaOH and 0.5 mN phenyl methyl sulfonyl fluoride were added to each well that cell culture media was eliminated and then maintained for 30 minutes at 60° C. to lyse the cell walls. The culture media at each well were placed into a dialysis tube of which one end is sealed and then the other end was sealed. After dialysis was carried out for 24 hours in a cold buffer (Tris-HCl 0.05 mol/l, NaCl 0.2 mol/l, $CaCl_2$ 0.05 mol/l, phenylmethylsulfonyl fluoride 0.3 mN), each of 100 μl was taken and put into a counting vial to which 10 ml of scintillation cocktail was added. Radioactivity was determined for 1 minute with the liquid scintillation counter. In order to determine the amount the total synthesized intra- and intercellular collagen proteins, 100 μl of each of the cell culture media and cell homogenates that dialysis has been completed were taken and placed into a 1.5 ml microtube to which 100 μl of collgenase buffer (0.05 M Tris-HCl, 1 mM $CaCl_2$, 0.03 mM phenyl methyl sulfonyl fluoride), and 100 ppm collagenase enzyme were added. Then, the mixture was maintained for 3 hours at 37° C. to completely decompose collagen. In order to remove the proteins undecomposed, 500 μl of a solution containing 50% trichloroacetic acid and 1% tannic acid were added and then deposited for 30 minutes. The resulting mixture was then centrifuged for 5 minutes at 1000×g. 100 μl of the supernatant was taken and put into the counting vial to which 10 ml of scintillation cocktail was added. Radioactivity was determined for 1 minute with the liquid scintillation counter. The results are set forth in Table 29 below.

TABLE 29

| Ointment Composition | Radioactivity (unit: $cpm/10^6$ cells) | |
|---|---|---|
| | Example | Comparative Example |
| 2-1 | 2670 | 2750 |
| 2-2 | 3640 | 2740 |
| 2-3 | 2340 | 2540 |
| 2-4 | 4630 | 2640 |
| 2-5 | 2670 | 2630 |
| 2-6 | 4840 | 2620 |
| 2-7 | 2640 | 2610 |
| 2-8 | 5240 | 2640 |
| 2-9 | 2320 | 2570 |
| 2-10 | 5340 | 2630 |
| 2-11 | 2220 | 2620 |
| 2-12 | 5260 | 2630 |
| 2-13 | 2140 | 2650 |
| 2-14 | 5260 | 2630 |
| 2-15 | 3540 | 2590 |
| 2-16 | 4540 | 2630 |
| 2-17 | 4960 | 2650 |
| 2-18 | 5240 | 2640 |

In order to study the efficacy and effects of the compositions on collagen production by human fibroblast, the ointment compositions according to the present invention were treated with the cell culture media containing $^{14}C$-proline. As a result, it was revealed that the collagen synthesis promotion effect was increased as the concentration of extract of *Ulmus cortex* increases in the compositions of Examples 2-2, 4, 6, 8, 10 and 12 containing the extract of *Ulmus cortex* while there was no effect on the collagen synthesis promotion by the *Achyranthis radix* extract in the compositions according to Examples 2-3, 5, 7, 9 and 11 which contain the extract of *Achyranthis radix*. The compositions of Examples 2-13, 14, 15, 16, 17, and 18 which have both the extracts of the *Achyranthis radix* and *Ulmus cortex* showed that the collagen synthesis promotion effect has increased as the concentration of the extract of *Ulmus cortex* increases.

EXPERIMENTAL EXAMPLE 2-6

Clinical Tests on the Efficacy and Effects of the Dentifrice Compositions according to the Present Invention The dentifrice compositions according to the present invention were subjected to clinical tests against periodontal diseases as follows:

The volunteers for this test were selected from the patients suffering periodontal diseases having a regular set of teeth without any dental loss. A precise medical examination for oral cavity was carried out for a total of 120 patients selected. The volunteers' age ranged from 30 to 50 year old. The volunteers were divided into two groups (60 volunteers/group) containing each 30 patients according to an interval of 10 year age and the distinction of sex. The clinical tests were carried out for determining the therapeutic effects of the test group ointments (Examples 2-1 to 2-18) and the comparative test group ointment (Comparative Examples 2-1 to 2-18) on the periodontal diseases.

The grouped volunteers were educated for the oral health and a correct use of toothbrush and then subjected dental brushing with identical toothbrushes. After the early gingival index was scored for the volunteers, they were continuously provided with the test group ointments and the comparative test group ointments. A medical examination for oral cavity was carried out after one week, 1 month, 3 months and 6 months to score the gingival index. The gingivitis index was measured in a manner that periodontal probe is first inserted into gingival pockets and then the edge of each tooth was screened under the condition that any press is not imposed to each tooth. After 30 seconds, the status of bleeding was measured and scored based on the following criterion.

| Score | contents |
|---|---|
| 0 | No bleeding |
| 1 | Spot bleeding |
| 2 | Linear bleeding |
| 3 | Triangle type bleeding at dental crevice portion |
| 4 | Overall gingival bleeding |

The results are set forth in Table 31 below.

TABLE 31

| Ointment composition | Early | | 1 week later | | 1 month later | |
|---|---|---|---|---|---|---|
| | Ex. | Comp. Ex. | Ex. | Comp. Ex. | Ex. | Comp. Ex. |
| 2-1 | 1.09 | 1.04 | 1.21 | 1.45 | 1.42 | 2.54 |
| 2-2 | 1.03 | 1.06 | 1.36 | 1.37 | 1.52 | 2.42 |
| 2-3 | 1.04 | 1.08 | 1.27 | 1.38 | 1.38 | 2.48 |
| 2-4 | 1.07 | 1.05 | 1.34 | 1.36 | 1.48 | 2.49 |
| 2-5 | 1.09 | 1.07 | 1.24 | 1.41 | 1.34 | 2.43 |
| 2-6 | 1.04 | 1.06 | 1.28 | 1.40 | 1.32 | 2.44 |
| 2-7 | 1.06 | 1.06 | 1.22 | 1.41 | 1.24 | 2.45 |
| 2-8 | 1.06 | 1.04 | 1.26 | 1.39 | 1.30 | 2.43 |
| 2-9 | 1.07 | 1.06 | 1.20 | 1.40 | 1.18 | 2.43 |
| 2-10 | 1.08 | 1.07 | 1.25 | 1.38 | 1.36 | 2.42 |
| 2-11 | 1.08 | 1.07 | 1.18 | 1.43 | 1.18 | 2.45 |
| 2-12 | 1.06 | 1.08 | 1.20 | 1.39 | 1.32 | 2.46 |
| 2-13 | 1.07 | 1.05 | 1.18 | 1.40 | 1.25 | 2.43 |
| 2-14 | 1.06 | 1.05 | 1.15 | 1.38 | 1.21 | 2.42 |

TABLE 31-continued

| Ointment composition | Early | | 1 week later | | 1 month later | |
| --- | --- | --- | --- | --- | --- | --- |
| | Ex. | Comp. Ex. | Ex. | Comp. Ex. | Ex. | Comp. Ex. |
| 2-15 | 1.07 | 1.06 | 1.13 | 1.42 | 1.17 | 2.47 |
| 2-16 | 1.07 | 1.06 | 1.09 | 1.39 | 1.11 | 2.48 |
| 2-17 | 1.08 | 1.04 | 1.08 | 1.38 | 1.08 | 2.48 |
| 2-18 | 1.09 | 1.07 | 1.09 | 1.39 | 1.09 | 2.52 |

As can be seen from the above clinical tests, therapeutic effects on the periodontal diseases of the ointment compositions according to the present invention (Examples 2-1 to 2-18) containing the extract of *Achyranthis radix* which can inhibit the productions of IL-1β and prostaglandin which are inducers of the periodontal disease and inhibit the enzymatic activity of collagenase which inhibits the superoxide production and decomposes periodontal tissues or the *Ulmus cortex* extracts which can promotes collagen synthesis and inhibits the enzymatic activity of collagenase were shown to he superior to those of the compositions according to Comparative Examples 2-1 to 2-18 at the time lapse of from 1 week to 6 months. That is, the gingival index according to the compositions of the Comparative Examples have continuously increased from 1 month later while the ointment compositions developed by the present invention have markedly inhibited the occurrence the periodontal diseases and thus lowered the gingivial index even if time passed. The compositions of Examples 2-13, 14, 15, 16, 17, and 18 which contain both the extracts of the *Achyranthis radix* and *Ulmus cortex* showed a synergic effects on the inhibition of the periodontal diseases.

What is claimed is:

1. A composition for treating or preventing periodontal diseases which comprises an amount of (i) a lower alkyl alcohol extract or aqueous extract of *Achyranthis radix* (ii) a lower alkyl alcohol extract or aqueous extract of *Ulmus cortex* or (iii) a mixture of said extracts effective to reduce a gingival index.

2. The composition according to claim 1, wherein the amount of the sole extract ranges from 0.001 to 5% by weight and the amount of the extract in the mixture ranges from 0.002 to 10% by weight based on the weight of the total composition.

3. The composition according to claim 2, wherein the composition is prepared in the form of dentifrice.

4. The composition according to claim 3, further comprising an abrasive selected from the group consisting of calcium monohydrogen phosphate, precipitated silica and calcium carbonate in an amount of 20 to 60% by weight based on the weight of the total composition.

5. The composition according to claim 3, further comprising fluoride compound selected from the group consisting of sodium fluoride and disodium fluorophosphate in an amount of 0.01 to 2.0% by weight based on the weight of the total composition.

6. The composition according to claim 2, wherein the composition is prepared in the form of ointment.

7. The composition according to claim 6, further comprising a surfactant, a solubilizing agent, a wetting agent, an active component delivery agent, a buffer, a sweetener, and a flavor, and a mixture thereof.

8. The composition according to claim 7, wherein the surfactant is polyoxyethylene-polyoxypropylene copolymer in an amount of 5 to 30% by weight based on the weight of the total composition.

9. The composition according to claim 7, wherein the solubilizing agent is a $C_1$ to $C_4$ lower alcohol selected from the group consisting of methanol, ethanol, isopropanol, and butanol in an amount of 1 to 20% by weight based on the weight of the total composition.

10. The composition according to claim 7, wherein the wetting agent is selected from the group consisting of glycerine, sorbitol solution, Polyethylene glycol 200, Polyethylene glycol 400, Polyethylene glycol 600, Polyethylene glycol 1000, propylene glycol, Poloxamer 407, Myverol 18-99, and a mixture thereof in an amount of 5 to 40% by weight based on the weight of the total composition.

11. The composition according to claim 7, wherein the active component delivery agent is gelatine, pectin or a mixture thereof in an amount of 1 to 30% by weight based on the weight of the total composition.

12. The composition according to claim 7, wherein the buffer is selected from the group consisting of sodium dihydrogen phosphate, disodium hydrogen phosphate, sodium phosphate, citric acid, sodium citrate, phosphoric acid, hydrochloride, sodium hydroxide, sodium pyrophosphate, pyrophosphate and a mixture thereof, and the pH of the composition is adjusted to 5 to 8.

13. The composition of claim 1, wherein said lower alkyl alcohol is selected from the group consisting of methanol, ethanol, propanol and butanol.

14. A composition for treating or preventing periodontal diseases which comprises an amount of (i) a lower alkyl alcohol extract or aqueous extract of *Achyranthis radix*, (ii) a lower alkyl alcohol extract or aqueous extract of *Ulmus cortex* or (iii) a mixture of said extracts effective to inhibit production of interleukin-1β, superoxide and prostaglandin $E_2$ by mononuclear leukocytes.

15. The composition of claim 14, wherein said lower alkyl alcohol is selected from the group consisting of methanol, ethanol, propanol and butanol.

16. A composition for treating or preventing periodontal diseases which comprises an amount of (i) a lower alkyl alcohol extract or aqueous extract of *Achyranthis radix*, (ii) a lower alkyl alcohol extract or aqueous extract of *Ulmus cortex* or (iii) a mixture of said extracts effective to promote collagen synthesis by gingival fibroblasts and inhibit collagenase activity.

17. The composition of claim 16, wherein said lower alkyl alcohol is selected from the group consisting of methanol, ethanol, propanol and butanol.

* * * * *